(12) United States Patent
Bouchier et al.

(10) Patent No.: US 7,722,527 B2
(45) Date of Patent: May 25, 2010

(54) SURGICAL IMPLANTS AND RELATED METHODS

(75) Inventors: Mark S. Bouchier, Lakeville, MN (US); Robert E. Lund, St. Michael, MN (US); James A. Gohman, Plymouth, MN (US)

(73) Assignee: AMS Research Corporation, Minnetonka, MN (US)

( * ) Notice: Subject to any disclaimer, the term of this patent is extended or adjusted under 35 U.S.C. 154(b) by 1103 days.

(21) Appl. No.: 11/115,655

(22) Filed: Apr. 26, 2005

(65) Prior Publication Data

US 2005/0267325 A1  Dec. 1, 2005

Related U.S. Application Data

(60) Provisional application No. 60/583,146, filed on Jun. 25, 2004, provisional application No. 60/567,601, filed on May 3, 2004.

(51) Int. Cl.
*A61F 2/00* (2006.01)
(52) U.S. Cl. ............................................ 600/30; 600/37
(58) Field of Classification Search ................... 600/30, 600/37, 29, 16; 606/142, 99, 153, 185, 151, 606/232; 623/23.65, 11.11, 2.1; 128/885, 128/897, 898
See application file for complete search history.

(56) References Cited

U.S. PATENT DOCUMENTS

| | | | |
|---|---|---|---|
| 5,163,960 A | 11/1992 | Bonutti | |
| 5,167,665 A | 12/1992 | McKinney | |
| 5,326,205 A * | 7/1994 | Anspach et al. | ............... 411/43 |
| 5,464,424 A | 11/1995 | O'Donnell, Jr. | |
| 6,248,118 B1 | 6/2001 | Tanner et al. | |
| 6,443,988 B2 * | 9/2002 | Felt et al. | ................. 623/17.12 |
| 6,502,578 B2 | 1/2003 | Raz et al. | |
| 6,514,194 B2 * | 2/2003 | Schweich et al. | ............. 600/16 |
| 6,575,897 B1 | 6/2003 | Ory et al. | |
| 6,582,443 B2 | 6/2003 | Cabak et al. | |
| 6,592,515 B2 | 7/2003 | Thierfelder et al. | |
| 6,592,610 B2 | 7/2003 | Beyar | |
| 6,641,524 B2 | 11/2003 | Kovac | |
| 6,648,921 B2 | 11/2003 | Anderson et al. | |
| 6,884,212 B2 | 4/2005 | Thierfelder et al. | |
| 7,070,558 B2 * | 7/2006 | Gellman et al. | ................ 600/37 |
| 7,189,251 B2 * | 3/2007 | Kay | ........................... 606/232 |
| 2002/0147382 A1 | 10/2002 | Neisz et al. | |

(Continued)

FOREIGN PATENT DOCUMENTS

EP  0 571 686  12/1993

(Continued)

OTHER PUBLICATIONS

PCT International Search Report for PCT/US2005/014376.

(Continued)

*Primary Examiner*—John P Lacyk
(74) *Attorney, Agent, or Firm*—Jose W. Jimenez; Kimberly K. Baxter; Gregory L. Koeller

(57) ABSTRACT

The invention relates to implantable surgical articles, particularly those useful for pelvic health, and related methods of making and using the articles, wherein the implantable articles include a rivet to attach materials together.

35 Claims, 12 Drawing Sheets

U.S. PATENT DOCUMENTS

| | | |
|---|---|---|
| 2003/0023137 A1* | 1/2003 | Gellman .................... 600/30 |
| 2003/0130670 A1 | 7/2003 | Anderson et al. |
| 2003/0171644 A1 | 9/2003 | Anderson et al. |
| 2003/0176875 A1 | 9/2003 | Anderson et al. |
| 2003/0225424 A1 | 12/2003 | Benderev |
| 2004/0015057 A1 | 1/2004 | Rocheleau et al. |
| 2004/0039453 A1 | 2/2004 | Anderson et al. |
| 2004/0220591 A1 | 11/2004 | Bonutti |
| 2004/0225181 A1* | 11/2004 | Chu et al. .................... 600/37 |
| 2005/0004426 A1* | 1/2005 | Raz et al. .................... 600/31 |
| 2005/0148815 A1* | 7/2005 | Mortier et al. ................ 600/37 |
| 2005/0245787 A1* | 11/2005 | Cox et al. .................... 600/37 |

FOREIGN PATENT DOCUMENTS

| | | |
|---|---|---|
| WO | WO 98/40114 | 9/1998 |

OTHER PUBLICATIONS

Kobashi, K.C. et al., "A New Technique for Cystocele Repair and Transvaginal Sling: The Cadaveric Prolapse Repair and Sling (CaPS)," UROLOGY 56 (Supplement 6A), Dec. 2000.

* cited by examiner

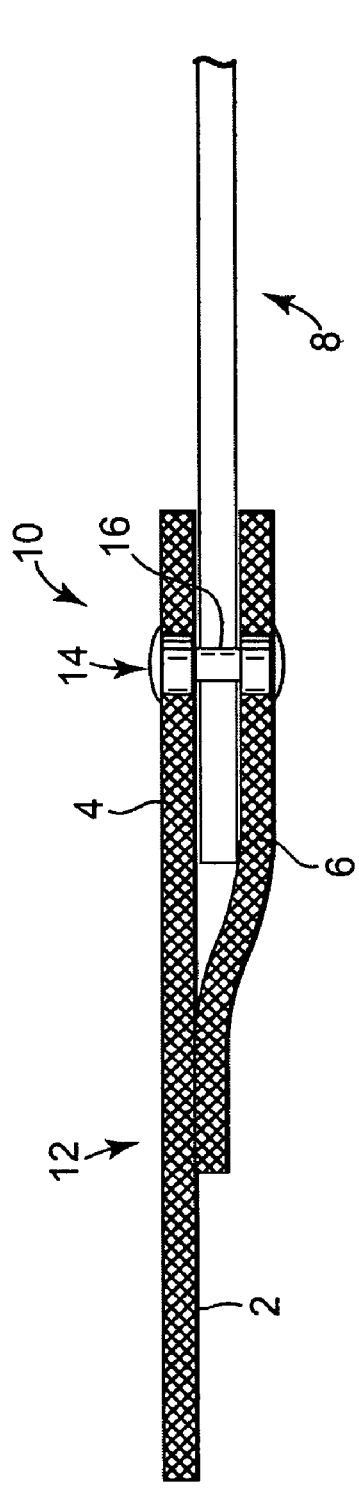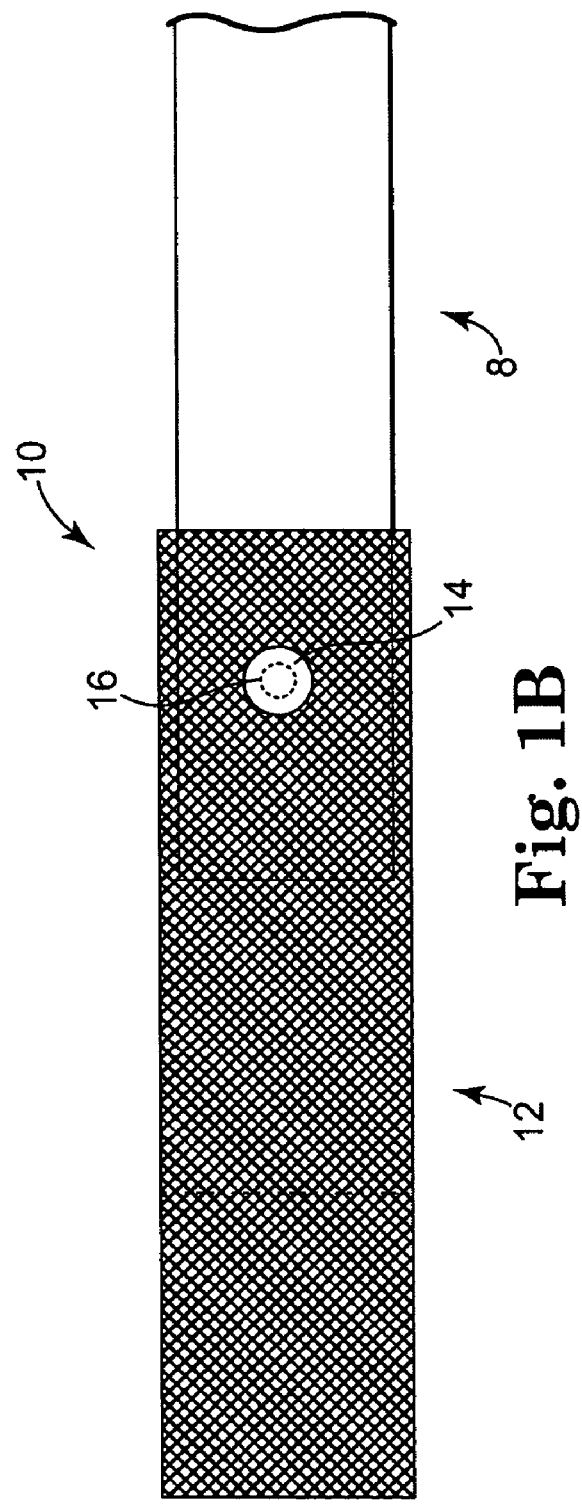

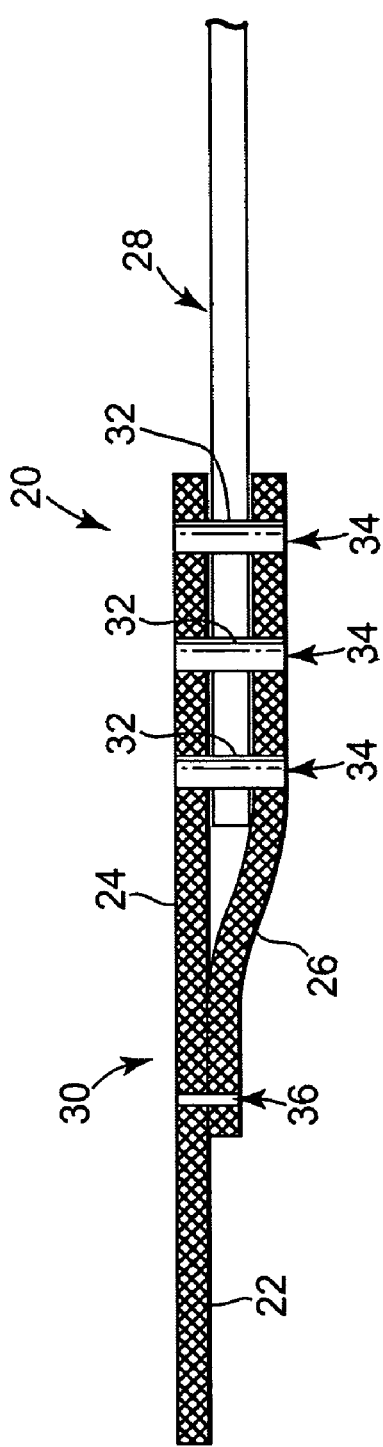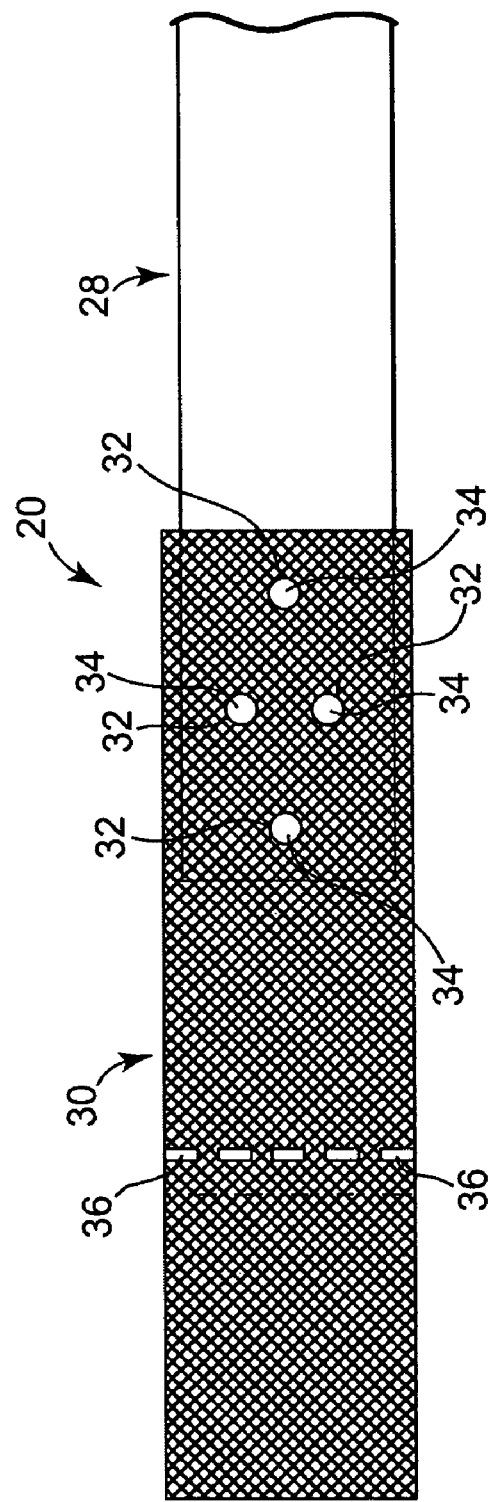
Fig. 2A
Fig. 2B

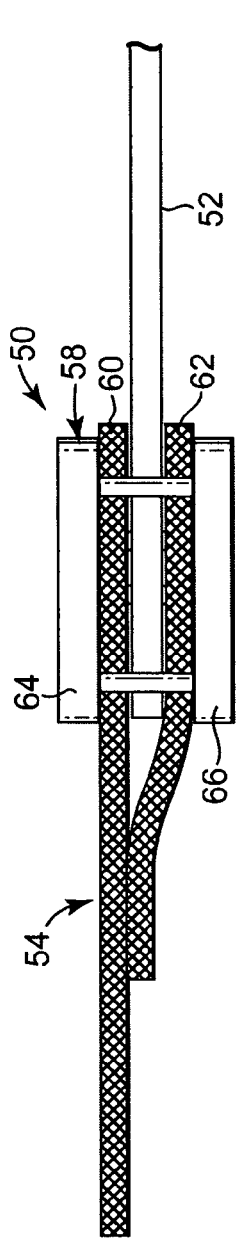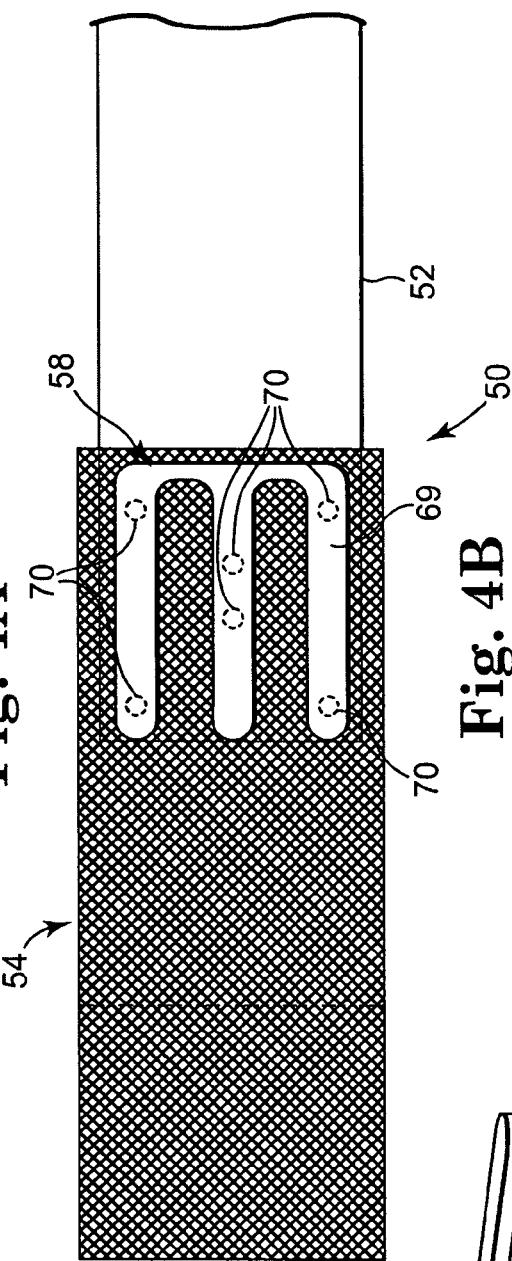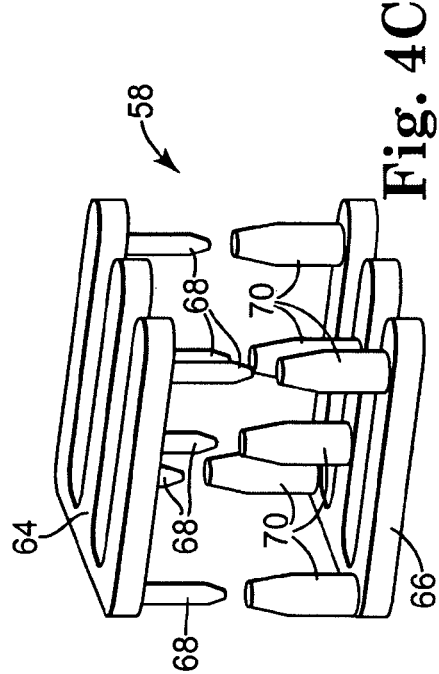

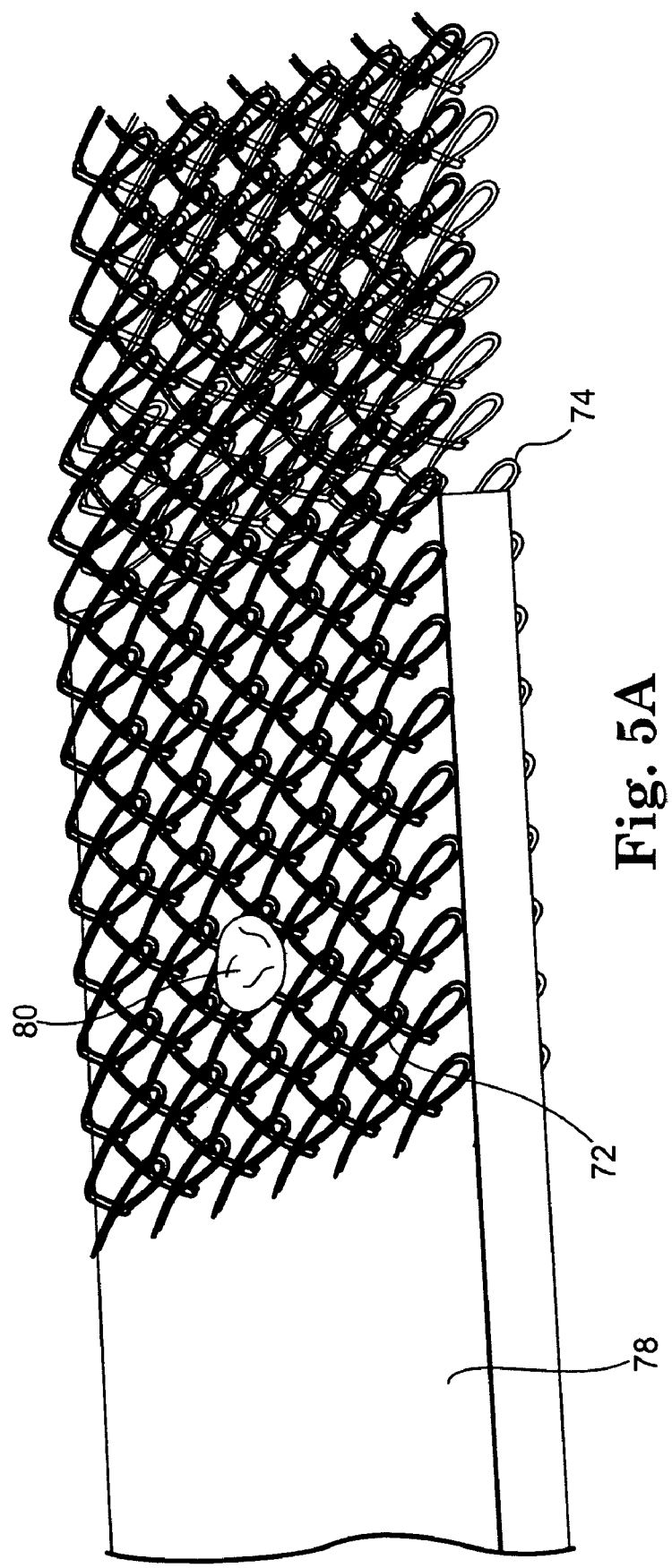

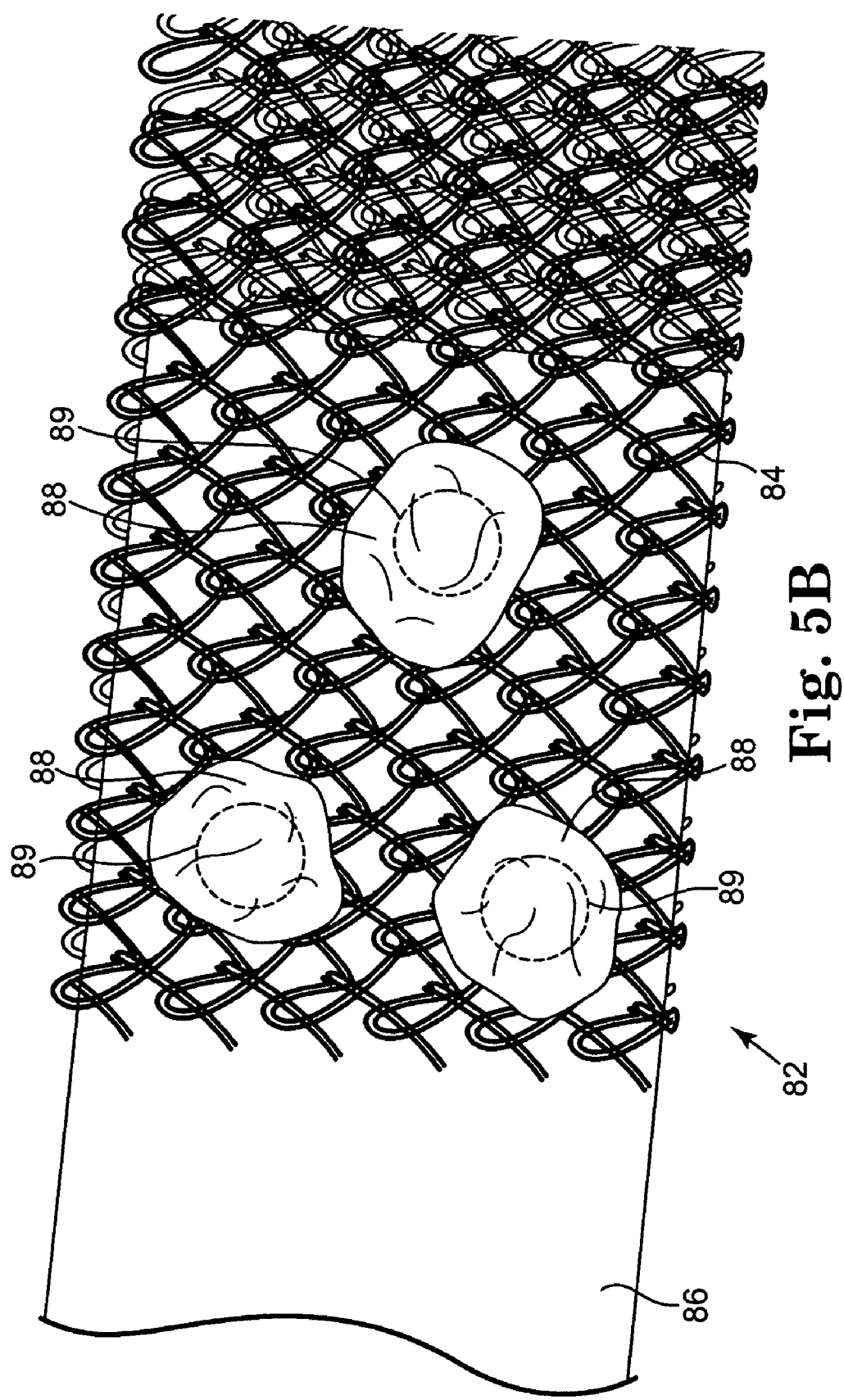

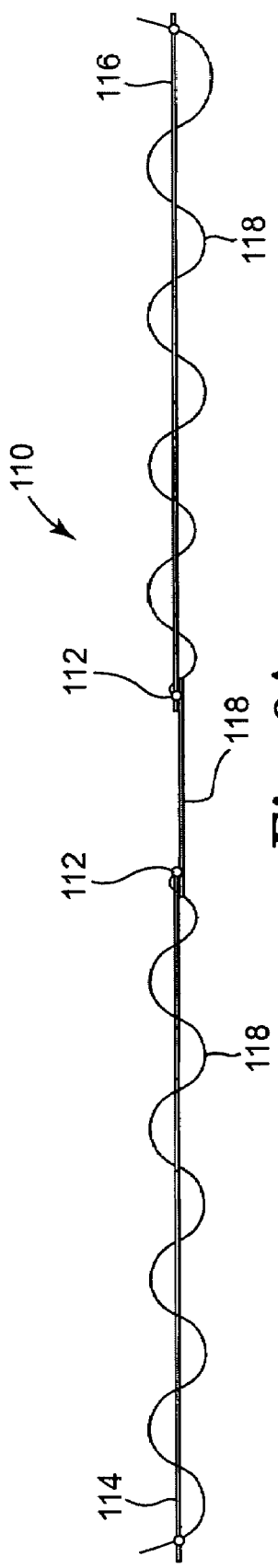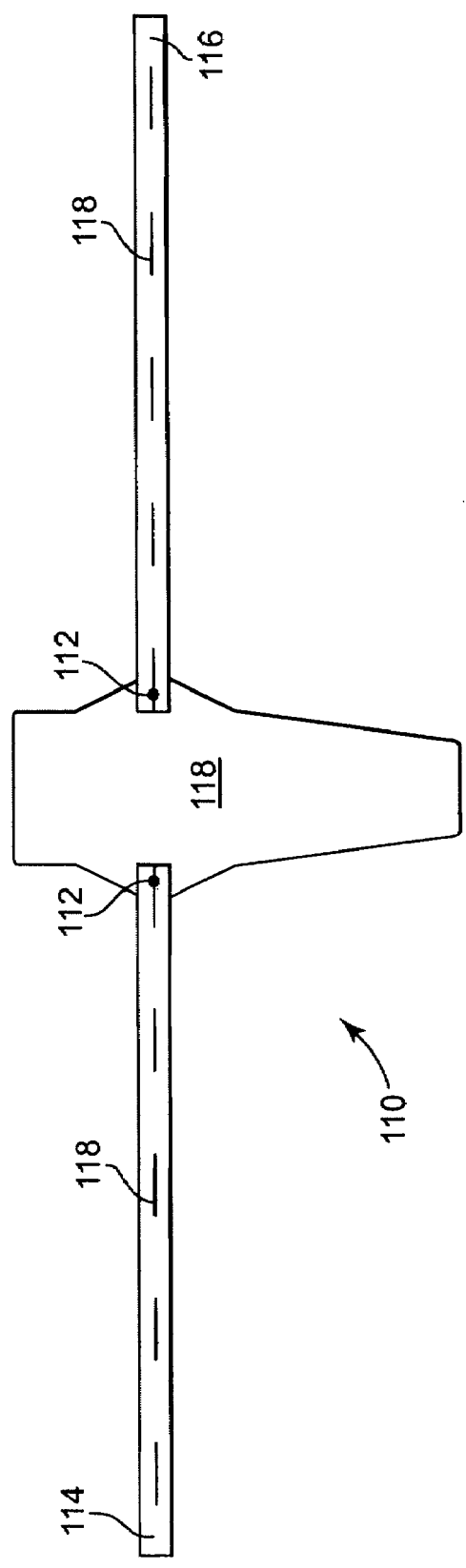

SURGICAL IMPLANTS AND RELATED METHODS

PRIORITY CLAIM

The present non-provisional patent Application claims benefit from United States Provisional Patent Application having Ser. No. 60/583,146, filed on Jun. 25, 2004, by Bouchier et al., entitled POLYMER ATTACHMENT METHOD FOR IMPLANTABLE ARTICLES, IMPLANTABLE ARTICLES, AND METHODS, and from United States Provisional Patent Application having Ser. No. 60/567,601, filed on May 3, 2004, by Bouchier et al., entitled ATTACHMENT METHODS FOR CONNECTING BIOLOGIC TISSUE TO SYNTHETIC MESH USED IN FEMALE PELVIC HEALTH; both of these provisional patent applications are commonly owned by the owner of the present patent application and the entireties of both provisional patent applications are incorporated herein by reference.

FIELD OF THE INVENTION

The invention relates to implantable surgical articles, particularly those useful for pelvic health, and related methods of making and using the articles.

BACKGROUND

A very large number of medical conditions can be treated by the surgical installation of a synthetic or biologic implant, e.g., to affect or support internal tissue.

Pelvic floor disorders, for example, include conditions that may result from weakness or damage to normal pelvic support systems. The conditions may affect pelvic floor support tissues of the bladder, vagina, rectum, and urethra, and may result in symptoms ranging from general or specific discomfort, sexual dysfunction, fecal or urinary incontinence, or organ prolapse.

Forms of treatment of many surgical conditions, including but not limited to pelvic conditions such as prolapse and urinary or fecal incontinence, involve the use of surgical implants that are surgically installed to contact and correct the condition of the tissue. For treatment of pelvic conditions, an implant can be placed in the pelvic region to support pelvic tissue such as the urethra, rectum, or vagina. Other conditions, outside of the pelvic region, also can be treated by surgical implants installed at the relevant portion of anatomy. The implant products may be formed from pieces of synthetic or non-synthetic (biologic) materials, with the final shape and size of an implant being dependent on the type of condition that the implant is used to treat.

Many currently commercial implant products that are formed from two or more pieces of biologic or synthetic materials secure the pieces together by glues or sutures. These methods of assembling the implant do not always result in a secure joint or connection of the pieces of the implant. Further, different types of joints or connections such as sutures or glues may possibly be the cause of biological rejection of the implant following surgery, or even infection.

Some currently available implant products that are formed from two attached portions of material are not pre-assembled at the site of manufacture, and must be assembled by a surgeon prior to surgery. This attachment method can be both cumbersome to the surgeon and can be an unnecessary use of a surgeon's time.

SUMMARY

The invention relates to surgical devices (e.g., implants) that include two materials joined together using a rivet, e.g., a polymeric rivet. A rivet joins the materials together by being located within holes or interstices of the materials; at a surface of at least one of the materials (i.e., at a surface of the implant); and extending from the surface through the thickness of at least one of the materials. A rivet may optionally extend through the entire thickness of two or more implant materials or through a full thickness of an implant. A rivet may include a rivet shaft (e.g., a cylindrical shaft) extending through a thickness of implant material. Optionally, a rivet may include one or more rivet heads at either or both surfaces of the implant, a rivet head having a cross-sectional area that extends beyond the cross section of the shaft, e.g., that has a surface area that is greater than the cross-sectional surface area of the shaft.

The rivet material may be any useful material, such as a polymeric material. Examples of polymeric materials that can be used as a polymeric rivet material include polymeric thermoplastics; curable polymers such as air, chemical, and moisture curable materials; polymeric materials that can be join materials of an implant by mechanical manipulation, e.g., by being threaded, screwed, snapped, or crimped; and polymeric materials that can be joined by other processing techniques, such as mechanical welding.

The materials of a surgical implant that are joined together by the rivet can be materials from a single piece of an implant (i.e., the same piece of material folded together and joined). Alternately, the materials may be two separate pieces of the same, similar, or different types of materials.

The implant itself may be useful for use with any type of implant surgery that treats any particular condition, including but not limited to general and specific conditions relating to pelvic tissue prolapse. Many implant products are presently available commercially that include two materials joined together by adhesives or sutures, e.g., from American Medical Systems Inc., of Minnetonka Minn. Examples of such products that join biologic tissue to a synthetic mesh material include: products from the BIOARC™ line of products such as BIOARC SP and BIOARC TO, available from American Medical Systems, Inc., for treating stress urinary incontinence; the PERIGEE™ product for treatment of cystocele, also from American Medical Systems, Inc.; the APOGEE™ product for treating enterocele, rectocele, and vaginal vault prolapse, also available from American Medical Systems Inc.; as well as products for CAPS procedures (combined-prolapse-repair-with sling) for treating cystocele and stress urinary incontinence. Examples of implant products that join two dissimilar synthetic materials include PERIGEE™ products having INTEPRO™ large pore polypropylene mesh attached to a polypropylene mesh of a different knit, for treating cystocele, available from American Medical Systems, Inc.; APOGEE products having INTEPRO large pore polypropylene mesh attached to a polypropylene mesh of a different knit, for treating enterocele, rectocele, and vaginal prolapse; and products useful for CAPS (combination prolapse repair with sling) procedures that include INTEPRO large pore polypropylene, for combination treatment of cystocele and stress urinary incontinence.

Still other products available from American Medical Systems include joining two polymeric materials to produce a "Y-mesh" joint that includes one material sandwiched between two pieces of another material. These products include, for example, the BIOARC™ SP & TO products and the Sacrocopoplexy Y-Mesh (STRAIGHT-IN™) products, as well as other graft-augmented repair procedures and implantable surgical devices.

In general, surgical implant devices such as those identified above may include a support portion that is sized and shaped to attach to internal tissue, connected (e.g., by a polymeric rivet as described) to extension portions (also referred to as, e.g., end portions or appendages) that may be shaped and sized to extend from the support portion to another location of the anatomy.

In some embodiments, a surgical implant may include additional features such as an anchoring suture that may be joined to a synthetic portion or a biologic portion, also attached by a polymeric rivet. For example, one or more of anchoring sutures could be joined to a thermoplastic (e.g., polypropylene) mesh material using, e.g., a thermoplastic or curable a polymeric rivet material. This could be accomplished by causing the polymeric rivet material to flow to contact both the suture and the mesh, and then the polymeric rivet material may be solidified or cured.

Still other examples of surgical implants could include other features, including, e.g., tips of extension portions that are adapted to fit a tool, such as an end of a needle, to allow the tool to push or pull the extension during a surgical installation procedure. Examples of such tips are sometimes referred to as dilators. Optionally or additionally, an implant may include a plastic sheath that covers an extension portion for use during a surgical installation procedure.

The use of a rivet, e.g., a polymeric rivet, to attach materials of an implant can allow for certain advantages in preparing or using the implant. For implants that include a biologic material, the biologic material can be lyophilized or hydrated when attached. For particular embodiments, attachment forces by use of a polymeric rivet can be more consistent (e.g., compared to forces produced using a suture), or, attachment forces may be stronger and may approach or exceed the strength of a biologic or mesh implant material. Further, when a suture is used to secure implant materials, the head of the knot may produce tissue irritation when the implant is installed. A rivet, on the other hand, would not include a knot head and may reduce inflammatory tissue response.

Further, surgical implants that include a rivet as described herein can be pre-assembled and then sold or otherwise supplied to a surgeon, meaning that the device is assembled to a condition where only minimal preparation (if any at all) needs to be performed by the surgeon prior to implantation. Minimal preparation may include modification to size or shape, or removing loose material, but does not include any significant step of assembly such as attaching one part of a device (e.g., a mesh) to another (e.g., biologic material), e.g., by use of sutures.

The invention additionally relates to methods of preparing these surgical devices, and methods of using these devices in surgical procedures.

In general methods of preparing a surgical implant can be accomplished by contacting implant materials in a manner by which apertures of the materials can be aligned to allow a rivet material to be inserted into or through the apertures. The rivet material may be a solid material or a fluid (e.g., flowable or liquid), when inserted into the apertures. The rivet material is then processed to join the materials together. Processing a rivet material that is fluid (e.g., a fluid polymeric rivet material) when inserted into the interstices may include causing the fluid polymeric material to solidify, e.g., based on reducing the temperature of the material or causing the flowable polymeric material to cure or harden due to, e.g., exposure to chemical treatment, moisture, catalyst, or radiation. Processing a rivet material that is solid when inserted into interstices of an implant material may include, e.g.,: mechanical manipulation by screwing, forming, crimping, folding, or sonic welding.

The invention additionally relates to apparatus for producing implants, such as an insert mold, optionally in combination with an injector for injecting a fluid rivet material into interstices of implant materials. An example of an insert mold can include closeable surfaces adapted to contain materials of a surgical implant. A surface of the mold includes an injection port. One or more gaskets located to define a space within the mold, near the injection port, can define a space within which a rivet can be formed from a flowable rivet material.

The implants may be used to treat any medical condition that is treatable by installation of a surgical implant of the type described herein, including material joined together by a rivet (e.g., a polymeric rivet). Examples of medical conditions that mat be treated include conditions of pelvic tissue prolapse, but other medical conditions may also be treated by implants as described, that include a rivet to attach implant materials together.

An aspect of the invention relates to a surgical implant that includes implant materials joined by a polymeric rivet. The polymeric rivet is located within apertures of the materials and extends from a surface of the implant through a thickness of at least one of the materials.

Another aspect of the invention relates to a surgical kit that includes a surgical implant and an insertion tool, the implant includes materials joined by a rivet, e.g., a polymeric rivet.

Another aspect of the invention relates to a method of preparing a surgical implant. The method includes: providing portions of implant material, each portion comprising an aperture, contacting the portions of implant material with the apertures aligned, inserting a rivet (e.g., a polymeric rivet) from a surface of either implant material, the rivet extending into the apertures, and processing the rivet to join the implant materials.

Another aspect of the invention relates to a method of preparing a surgical implant. The method includes: providing a support portion comprising a support portion aperture, providing an extension portion comprising an extension portion aperture, contacting the extension portion and the support portion with aligned extension portion aperture and support portion aperture, inserting a rivet material (e.g., a polymeric rivet material) from a surface of either the extension portion or the support portion, the rivet material extending into the extension portion aperture and the support portion aperture, and processing the rivet material to attach the extension portion to the support portion.

Another aspect of the invention relates to an insert mold adapted to assemble materials of a medical implant. The comprising includes: closeable surfaces sized to contain portions of implant material, each portion including an aperture; a surface that includes an injection port that can be aligned with the apertures; the mold further including a gasket, wherein when the closeable surfaces are closed to contain the implant material with aligned apertures, the gasket partially defines a space that contains the aligned apertures.

Yet another aspect of the invention relates to an insertion mold in combination with an injector. The injector operates at a temperature in the range from 350 to 500 degrees Fahrenheit; produces a single injection volume of injected material in the range from about 0.001 cubic centimeters to about 0.1 cubic centimeters, and includes an injection barrel having a diameter in the range from about 0.125 to 0.5 inches, and an injector nozzle having a diameter in the range from about range from about 0.01 to about 0.10 inches.

Yet another aspect of the invention relates to a method of producing a surgical implant. The method includes: providing an extension portion of an implant that includes an extension portion aperture; providing a support portion of an implant that includes a support portion aperture, using an insert mold such as described herein to contact the extension portion and the support portion with aligned extension portion aperture and support portion aperture; and using an injector assembly as described herein to inject flowable polymeric material into the extension portion aperture and the support portion aperture.

Yet another aspect of the invention relates to a surgical implant comprising implant materials joined by a rivet, the rivet extending from a surface of a the implant through apertures of at least two portions of implant material.

BRIEF SUMMARY OF THE DRAWINGS

FIG. 1A is a schematic, cross-sectional, cut-away side view of an embodiment of a portion of a surgical implant that includes a polymeric rivet.

FIG. 1B is a top view of an embodiment of a portion of a surgical implant that includes a polymeric rivet.

FIG. 2A is a schematic, cross-sectional, cut-away side view of an embodiment of a portion of a surgical implant that includes a polymeric rivet.

FIG. 2B is a top view of an embodiment of a portion of a surgical implant that includes a polymeric rivet.

FIG. 4A is a schematic, cross-sectional, cut-away side view of an embodiment of a portion of a surgical implant that includes a polymeric rivet.

FIG. 4B is a top view of an embodiment of a portion of a surgical implant that includes a polymeric rivet.

FIG. 4C is a schematic, perspective side view of an embodiment of an ultrasonically weldable coupler.

FIG. 5A is a schematic top perspective view of a polymeric rivet and implant according to the invention.

FIG. 5B is a schematic top view of a polymeric rivet and implant according to the invention.

FIG. 6 is a schematic top view of a pelvic implant of the invention that includes materials connected by a polymeric rivet.

FIG. 6A is a schematic side view of a pelvic implant of the invention that includes materials connected by a polymeric rivet.

DETAILED DESCRIPTION

Figure 3:
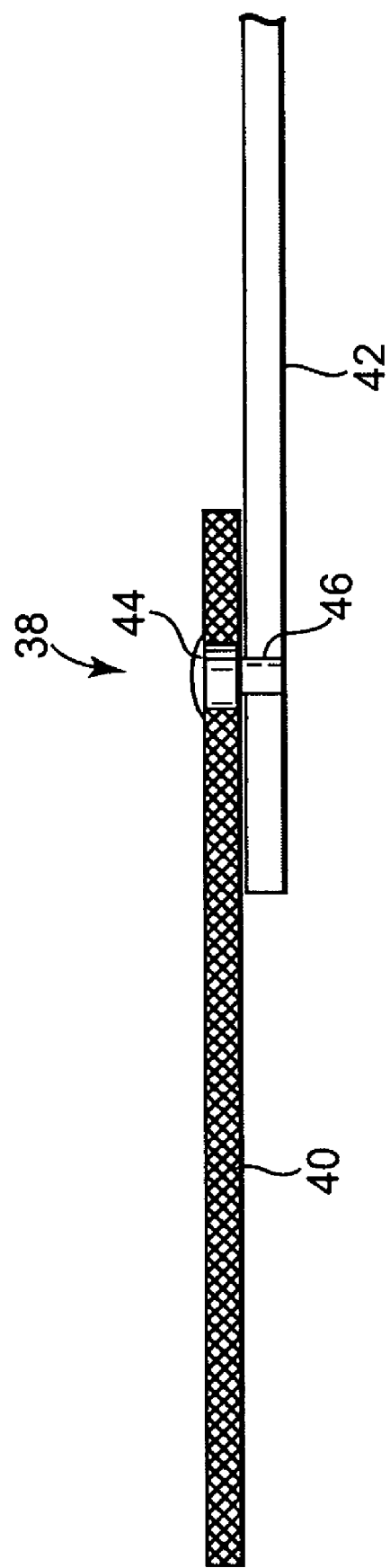
FIG. 3 is a schematic, cross-sectional, cut-away side view of an embodiment of a portion of a surgical implant that includes a polymeric rivet.

The invention involves surgical implants that include a rivet, e.g., a polymeric rivet, to attach or join materials of an implant together, e.g., one piece or portion of the implant to another piece or portion of the implant, or a single piece of an implant to itself, e.g., by folding.

The implants can be used to treat medical conditions including but not limited to conditions of the pelvic region. Implants can be installed into a patient to affect or to support tissue to treat various conditions such as any of a variety of pelvic prolapse conditions, as well as non-pelvic conditions. Examples of pelvic conditions that can be treated include urinary or fecal incontinence for men and women; prolapsed organs, e.g., vaginal prolapse in women such as cystocele, enterocele, rectocele and vaginal vault prolapse; among others.

Some examples of surgical implants useful for treating pelvic conditions include supportive implants such as vaginal supports to treat vaginal prolapse; urethral slings to treat male or female incontinence; and rectal supports to treat fecal incontinence. Some such examples and related methods are described, for example, in Assignee's copending patent applications, including U.S. application No. 2004/0039453 "Pelvic Health Implants and Methods," having Ser. No. 10/423,662, and filed on Apr. 25, 2003; U.S. application "Method and Apparatus for Treating Pelvic Organ Prolapse," having Ser. No. 10/834,943, and filed on Apr. 30, 2004; and U.S. application No. 2003/0171664 "Transobturator Surgical Articles and Methods," having Ser. No. 10/306,179, and filed on Nov. 27, 2002; the entireties of each of these patent publications being incorporated herein by reference.

Various examples of surgical implants are known and commercially available for treatment of pelvic conditions including those sold by American Medical Systems, Inc., of Minnetonka Minn., under the trade names APOGEE™, PERIGEE™, SPARC®, MONARC™, and BIOARC™. The attachment methods described herein can be used with these and other medical implants.

A material of an implant, attached using a rivet, may be a biocompatible material such as a biologic material or a synthetic material such as a polymeric or other non-biologic material. The materials that are joined may be, e.g., two different portions of the a single piece of an implant (e.g., a single piece of material folded so that two portions contact each other); or the materials may be two portions different pieces of material that can be the same material, similar types of different materials (e.g., two different polymeric mesh materials), or two different materials such as a polymeric mesh or film and a biologic material.

A synthetic implant material can be any synthetic material that can be useful in an implantable surgical device, such as a biocompatible polymeric material or a biocompatible non-polymeric synthetic material. Examples of useful polymeric materials include thermoplastic polymeric materials such as polyolefins (e.g., polypropylenes), polyurethanes, acetel materials, Teflon® materials, and the like; thermoset materials such as silicones; and materials that are otherwise curable, e.g., that can be cured by ultraviolet radiation or chemical reactions, including curable materials such as curable urethanes, epoxies, acrylates, cyanoacrylates, and the like. Any of these materials may be homopolymers, copolymers, or a blend or other combination of homopolymers, copolymers, or both. Other suitable synthetic materials include metals (e.g. silver filigree, tantalum gauze mesh, and stainless steel mesh).

A synthetic implant material may be in any form, such as a continuous, solid, or semi-continuous (e.g., perforated) film; or in the form of combined fibers or strands, e.g., a braided, knit, tied, mesh, woven, non-woven, or fabric-type of material; or combinations of these. Certain embodiments of implants include a synthetic implant portion in the form of a polymeric mesh material. The mesh material includes one or more woven, knitted or inter-linked polymeric filaments or fibers that form multiple fiber junctions throughout the mesh. The fiber junctions may be formed via weaving, knitting, braiding, joining, ultrasonic welding or other junction forming techniques, including combinations thereof, leaving openings or pores ("interstices") between elements of the fibers. The size of the interstices mesh may be sufficient to allow tissue in-growth and fixation within surrounding tissue.

Many different types of synthetic film and mesh materials are known and may be suitable for use as a portion or piece of an implant. These materials may be prepared from biocompatible materials that may be bioabsorbable or non-bioabsorbable, e.g., in the form of mesh materials. Suitable materials include cotton, linen, silk, polyamides (polyhexamethylene adipamide (nylon 66), polyhexamethylene sebacamide (nylon 610), polycapramide (nylon 6), polydodecanamide (nylon 12), and polyhexamethylene isophthalamide (nylon 61), and copolymers and blends thereof), polyesters (e.g., polyethylene terephthalate, polybutyl terephthalate, copolymers and blends thereof), fluoropolymers (e.g., polytetrafluoroethylene and polyvinylidene fluoride), polyolefins (e.g., polypropylene, including isotactic and syndiotactic polypropylene and blends thereof, as well as blends composed predominantly of isotactic or syndiotactic polypropylene blended with heterotactic polypropylene, and polyethylene), silicone, polygalactin, Silastic, polycaprolactone, polyglycolic acid, poly-L-lactic acid, poly-D-L-lactic acid and polyphosphate esters.

Commercial examples of non-absorbable polymeric materials for use in an implant include MARLEX (polypropylene) available from Bard of Covington, RI; PROLENE (polypropylene) and PROLENE Soft Polypropylene Mesh or Gynemesh (nonabsorbable synthetic surgical mesh), both available from Ethicon, of New Jersey; MERSILENE (polyethylene terephthalate) hernia mesh also available from Ethicon; GORE-TEX (expanded polytetrafluoroethylene) available from W. L. Gore and Associates, Phoenix, Ariz.; INTEPRO™ polypropylene materials, and the polypropylene material used in the commercially available SPARC® sling system, each available from American Medical Systems, Inc. of Minnetonka, Minn. Commercial examples of absorbable materials include DEXON (polyglycolic acid) available from Davis and Geck of Danbury, Conn., and VICRYL available from Ethicon.

Suitable non-synthetic (biologic) implant materials include allografts, homografts, heterografts, autologous tissues, cadaveric fascia, autodermal grafts, dermal collagen grafts, autofascial heterografts, whole skin grafts, porcine dermal collagen, lyophilized aortic homografts, preserved dural homografts, bovine pericardium, and fascia lata. A biologic material may be in any form desired based on the type of surgical implant. Examples include sheet-like pieces that can form a portion of a surgical implant such as a sling.

According to the invention, materials of an implant are joined together using a rivet. The rivet can be used to join together two different materials, two of the same materials, or portions of the same single piece of implant material; e.g., to join a synthetic material to a biologic material or to join two synthetic materials together.

A "rivet" is a material that connects implant materials, e.g., pieces or portions of an implant, together, by being located within holes or interstices of the materials and extending through the thickness of at least one of the materials, e.g., through the entire thickness of two or more pieces of an implant, or through the full thickness of an implant. A rivet may include a shaft located within interstices of implant materials and extending through the full thickness or thicknesses of one or more implant material or materials. A shaft may be cylindrical or of another useful shape. A rivet may optionally include one or more rivet heads at either or both surfaces of an implant, a rivet head having a cross-sectional surface that extends beyond the cross-sectional surface of a shaft of the rivet, e.g., a rivet head surface that has a greater cross-sectional surface area (e.g., from 2 to 5 times greater) compared to cross-sectional surface area of the rivet shaft.

An "aperture" of an implant material is a hole or interstice present in a material of the implant. Exemplary apertures include the interstitial spaces between a mesh, as well as a formed aperture or hole that may be formed in a film or a mesh material by any method, such as by the use of a punch, drill, cutting tool, etc. A rivet may be placed by various methods within holes or interstices of the materials, e.g., depending on the nature of the holes or interstices or depending on the manner of formation of a rivet. For example, a polymeric rivet may be place to fill and extend through a hole that has been pre-formed (e.g., punched) in a solid or semi-solid film material. Alternately, a polymeric rivet material may be placed in the space of more than a single interstice of a mesh material, and may cover or coat one or multiple strands of a mesh material, optionally without completely filling in an interstice of a material.

A rivet may be prepared from any material that can be formed to be located in holes or interstices of implant materials, such as a polymeric material. A rivet material can be a biocompatible polymeric material that is, e.g., a thermoplastic polymer material; a curable polymer such as a chemically curable, energy-curable, or heat-setting (thermosetting) polymer; a room temperature solid plastic material that can be ultrasonically welded; or a room temperature plastic material that can be mechanically secured or fastened (e.g., snapped or threaded together, crimped, bent, or otherwise formed to produce a mechanical polymeric rivet attachment). A material used for a rivet may the same or different from a polymeric material of the implant itself.

Examples of useful polymeric thermoplastic materials include polyolefins (e.g., polypropylenes), polyurethanes, acetels, Teflon® materials, and the like. For thermoplastic materials, the processing temperature can be selected to provide a secure riveted joint between materials of an implant, but to also avoid damage to implant material during processing the polymeric rivet. Particularly useful materials (e.g., thermoplastic materials) useful as polymeric rivet materials can be have a processing temperature that does not damage material or materials of an implant. A "processing temperature" is a temperature at which a polymeric rivet material must achieve during processing of the polymeric rivet to attach the materials of the implant. A processing temperature may refer to an elevated temperature at which, e.g., a thermoplastic material may become sufficiently flowable to be formed into a rivet. Typically, a thermoplastic rivet material may have a processing temperature that will allow for flow of the thermoplastic material, and injection of the material into interstices of implant materials. A thermoset (e.g., chemically or otherwise curable) may have a processing temperature that is about room temperature, e.g., the thermosetting polymer is sufficiently fluid at room temperature to be injected into interstices of implant material.

For thermoplastic rivet materials, desirable ranges for processing temperatures above room temperature may differ depending on the materials of an implant that are being joined together, e.g., synthetic materials, biologic materials, etc. To use a thermoplastic rivet material to join materials of an implant that include a biologic material, while preventing damage or degradation of a biologic material, a thermoplastic rivet material can have a processing temperature that does not denature proteins contained in the biologic material. A temperature that is sufficiently low to avoid denaturing of proteins of a biologic material will depend on factors such as the relative amount of material applied to an amount of biologic material and the heat capacities of each of the biologic material and the thermoplastic rivet material. Generally speaking, for polypropylene rivet materials, a desired temperature range can be from 350 degrees F. to about 500 degrees F., e.g., below about 410 degrees F., or from about 380 degrees F. to about 440 degrees F.

For an implant that includes a synthetic polymeric material, a polymeric rivet material may be used that has a processing temperature that is below a temperature that will damage the synthetic polymeric material, and, optionally, that is below a temperature that would cause the polymeric material to melt. Optimally, when a thermoplastic rivet material is applied to a polymeric mesh, the polymeric mesh can be exposed to a heated thermoplastic rivet material without suffering any degradation, but the thermoplastic rivet material can be melted to flow between interstices of the polymeric mesh material to contact strands of the mesh and produce a mechanical join upon solidifying. The rivet may fill an interstice or may flow around strands to, e.g., cover, coat, or encase one or more strands of a polymeric mesh to produce a mechanical join, and may or may not necessarily fill the space of an interstice or hole.

Examples of chemically curable and thermosettable polymeric materials include materials that are understood to cure based on the presence of moisture, air, or catalyst. Examples include homopolymers, copolymers, and blends of one or more acrylates, cyanoacrylates, epoxies, silicones, and the like. These materials may be homopolymers, copolymers, or a blend or other combination of homopolymers or copolymers. Thermosettable polymeric rivet materials may be flowable (e.g., liquid) at room temperature, and can be chemically cured or may be cured by exposure to heat or other energy, such as electromagnetic energy, UV energy, e-beam energy.

Examples of ultrasonically weldable plastic materials may include polyolefins (e.g., polypropylene), polycarbonates, nylons, and the like. These materials are generally rigid plastic at room temperature and can be shaped and sized to fit together to form a mechanical bond. For example, two portions of an ultrasonically weldable rivet coupler can contain opposing frames members that fit against opposing surfaces of an implant, while one or multiple opposing posts extend from the frame, through interstices of implant material. The opposing posts can include, e.g., channels, holes, or other features having sizes and shapes to engage an opposing post to produce a mechanical bond such that the frames contact the surfaces of the implant materials to secure the materials together. As an example, a post may include a channel or hole into which an opposing post fits to produce a mechanical, frictional attachment. The rigid plastic of the ultrasonically weldable rivet coupler can be placed together in frictional contact, with the posts extending through interstices of implant material, and then exposed to ultrasonic energy upon which exposure the plastic will experience melting and contacting pieces of the weldable plastic material (e.g., posts) will be welded together to attach the materials of the implant together.

Another type of polymeric rivet is a mechanical plastic fastener that can be used to join materials of an implant together based on mechanical interaction of elements of the mechanical fastener. Examples of mechanical plastic fastener are plastic pieces that can be solid (e.g., rigid) materials at room temperature, for insertion into interstices of implant material. The mechanical fastener can include one or two or more pieces or portions that are shaped to fit together and secure to each other, with material of the implant located between pieces or portions of the fastener. The mechanical fastener may secure implant materials based on mechanical interactions such as friction produced between two threaded pieces; by friction between two pieces that mechanically snap together; by mechanically crimping or bending a polymeric material; or by otherwise forming a polymeric mechanical rivet to join together implant materials.

The attached figures illustrated examples of rivets as described. FIG. 1A shows implant 10 (e.g., a urethral sling, vaginal support, or other pelvic tissue support) that includes synthetic "Y-mesh" piece 12 attached to biologic material 8. Y-mesh piece 12 includes portions 2, 4, and 6. Portions 4 and 6 overlap opposing surfaces of a portion of biologic material 8 that includes aperture 16 that has been previously punched or drilled through the biologic material. Polymeric rivet 14, e.g., of a thermoplastic polymeric rivet material such as a polypropylene, has been melted and solidified in a manner whereby polymeric rivet 14 extends from surfaces of each portion 4 and 6 of mesh materials, and through aperture 16 of biologic material 8. As such, polymeric rivet 14 is located within interstices of Y-mesh portion 4, extends continuously through aperture 14 of biologic material 8, and then further extends to interstices of Y-mesh portion 6. Rivet 14 includes two polymeric rivet heads formed at each opposing surface of implant 20. By this construction, polymeric rivet 14 connects both of Y-mesh portions 4 and 6 to biologic material 8.

Still referring to FIGS. 1A and 1B, Y-mesh portions 2 and 4 of device 10 are illustrated as a continuous strip of mesh to which Y-mesh portion 6 is attached. Portion 6 can be attached to portions 2 and 4 by any technique, such as by use of a suture material to stitch and tie the portions together, an adhesive, or, by use of a polymeric rivet such as a thermoplastic material as described herein (none of these is shown in FIGS. 1A and 1B). Combinations of suture materials, adhesives, and joining by use of a polymeric rivet as described, can also be useful.

FIG. 1B schematically illustrates a top view of the portion of the implant of FIG. 1a. FIG. 1B illustrates polymeric rivet 14 at an approximately central location of an end of biologic material 8, whereby polymeric rivet 14 connects top Y-mesh portion 4, through aperture 12 in biologic 8, to bottom Y-mesh portion 6 (not visible from this top view).

FIGS. 2A and 2B (side, cross-sectional view and top view, respectively) schematically illustrate another embodiment of a polymeric rivet, which is illustrated to join materials of implant 20. Implant 20 may be any implant for use to treat a pelvic tissue conditions. FIGS. 2A and 2B show a synthetic "Y-mesh" 30 that includes portions 22, 24, and 26. Portions 24 and 26 overlap opposing surfaces of a portion biologic material 28 that includes four (4) apertures 32. Polymeric rivets 34, e.g., of thermoplastic polymeric material such as a polypropylene, have been melted and solidified in a manner whereby the polymeric material is located within interstices of mesh portion 24, extends continuously through apertures 32 of biologic material 28, and extend into interstices of mesh portion 26. Rivets 34 do are illustrated to not include rivet heads, but rivet heads may optionally be included if desired. By this construction, polymeric rivets 34 act to connect portions 24 and 26 of Y-mesh 30 to biologic material 28.

Still referring to FIGS. 2A and 2B, Y-mesh portions 22 and 24 are illustrated as a continuous strip of mesh to which Y-mesh portion 26 is attached. Portion 26 can be attached to continuous portion 22 and 24 of Y-mesh 30 by any bonding or joining technique, such as by use of a suture material to stitch and tie the portions together, an adhesive, or, according to the present description, by use of a synthetic (e.g., polymeric) polymeric rivet material such as a thermoplastic material. Combinations of suture materials, adhesives, and joining by use of a polymeric rivet as described, can also be useful.

As shown in FIGS. 2A and 2B, device 20 includes bonds 36 that attach an end of portion 26 to continuous portions 22 and 24. Bonds 36 are shown as extending laterally, discontinuously, from one side to the other of the device 20. As illustrated, Y-mesh 30 can be considered to be made of thermoplastic (e.g., polypropylene) mesh material. Bonds 36 may be formed by heating the thermoplastic (e.g., polypropylene) material of Y-mesh 30 to melt the material, while placing pressure on the melted materials, then allowing the materials to cool. According to alternate embodiments, a flowable polymeric rivet material (thermoplastic, thermoset, or otherwise) could be inserted into apertures of mesh materials of Y-mesh 30, and then solidified, cured, or otherwise processed, to join the materials together. If desired, a suture or other stitched, sewn, or woven material may optionally or additionally be used to join portions of mesh materials to assemble Y-mesh 30.

FIG. 2B schematically illustrates a top view of the implant 30 of FIG. 2A. FIG. 2B illustrates polymeric rivets 34 within apertures 32 spaced over an area of biologic 28, whereby polymeric rivets 34 connect top portion 24 of Y-mesh 30, through apertures 32 of biologic material 28, to bottom portion 26 of Y-mesh 30.

FIG. 3 illustrates another embodiment of a surgical implant that includes a polymeric rivet. FIG. 3 is a side, cross-sectional view of implant 38, having mesh portion 40 joined to biologic portion 42 by polymeric rivet 44. Implant 38 may be an implant for use to treat a pelvic tissue conditions. Polymeric rivet 44, e.g., a flowable thermoplastic (e.g., polypropylene) or thermosetting polymeric material, has been injected into interstices of biologic material 42 (aperture 46) and into interstices of mesh 40. Following injection into interstices, the flowable polymeric material was solidified in a manner whereby the polymeric rivet is located within interstices of mesh portion 40 and extends continuously through aperture 46 of biologic material 42. Rivet 44 includes a rivet shaft located within interstices of implant materials 40 and 42, and two rivet heads located at opposing exterior surfaces of implant 38. By this construction, polymeric rivet 44 secures mesh 40 to biologic material 42.

FIGS. 4A, 4B, and 4C, illustrate implant 50 that includes biologic material 52 joined to Y-mesh 54 by polymeric rivets in the form of ultrasonic weld coupler 58. Implant 50 may be any form of surgical implant such as a pelvic implant. Implant 50 includes biologic portion 52 between two portions 60 and 62 of synthetic mesh. Ultrasonic weld coupler 58 includes top and bottom frames 64 and 66, which are "E" shaped when viewed from the top. Each of frames 64 and 66 also includes posts 68 and 70 extending perpendicular from the frame and sized and shaped to insert through interstices of biologic material 52 and mesh portions 60 and 62, and then to mechanically fit together in frictional contact. According to the illustrated example, posts 68 of upper frame 64 are circular interior posts having length and diameter to fit within apertures of exterior posts 70 of lower frame 66. These posts are an illustrative polymeric rivet configuration, and other configurations of various post sizes, shapes, arrangements on frames, and numbers will be appreciated. For instance, while 6 opposing posts are illustrated to produce 6 polymeric rivets, more or fewer than 6 posts or rivets may be desired or useful.

When "E" shaped frames 64 and 66 are brought together to contact mesh portions 60 and 62, posts 68 and 70 extend between apertures of mesh portions 60 and 62, and biologic material 52. Frames 64 and 66 contact exterior surfaces of mesh portions 60 and 62, to mechanically join mesh portions 60 and 62 with biologic material 52 between.

FIG. 4B, a top view of implant 50, illustrates frame 64 in contact with mesh portion 60. The locations of posts 70 are also illustrated.

FIG. 4C is a side perspective view of frames 64 and 66 of ultrasonic weld coupler 58, which includes interior rivets or "shafts" 68 and exterior rivets or "posts" 70. As show in FIG. 4C, top frame 64 includes six shafts or inner rivets 68 extending generally in a perpendicular fashion from frame 64. Each of inner rivets 68 fit into apertures of outer rivets or posts 70, which extend from frame 66 in opposition to frame 64. In general, posts 70 can function as polymeric rivets to secure implant materials together by inserting inner rivet 68 through apertures of implant material and also inserting outer rivet 70 through apertures of implant material, optionally with additional pieces of implant material in-between. Inner posts 68 enter apertures of outer posts 70 to produce a frictional bond. Optionally, ultrasonic energy can be applied to the polymeric rivet material of inner posts and outer posts 68 and 70 to cause the polymeric material to melt and become welded together in position.

FIG. 5A illustrates details of an embodiment of a polymeric rivet according to the invention, polymeric rivet 80, joining polymeric mesh portions 72 and 74 of a surgical implant 76 to biologic portion 78. Referring to FIG. 5A, biologic material 78 includes a punched aperture (not specifically illustrated) at a central location of material 78. Synthetic (polymeric, such as polypropylene) mesh material portions 72 and 74 overlap opposing surfaces of biologic material 78, including the aperture. Polymeric material forms rivet 80 between interstices of mesh portions 72 and 74, and the aperture of biologic material 78. The material of polymeric rivet 80 can the same material as mesh the material of mesh portions 72 and 74, e.g. polypropylene, or may be different.

Rivet 80 can be formed using a flowable polymeric rivet material such as a thermoplastic polymer, thermosetting polymer, or otherwise curable polymer. For example, a thermoplastic synthetic polymeric rivet material may be made flowable at an elevated temperature, and the flowable material may be injected to flow into interstices of mesh materials 72 and 74, through the aperture (not specifically shown) of biologic material 78. Alternately, polymeric rivet 80 can be formed from a non-thermoplastic curable polymeric rivet material, e.g., at room temperature, by causing the flowable polymeric rivet material to flow into interstices of mesh materials 72 and 74, and through the aperture (not shown) in biologic material 78, followed by curing the polymeric material, e.g., by exposure to heat, radiation, catalyst, air, or moisture, etc.

FIG. 5B shows implant 82 that includes polypropylene mesh 84 joined to biologic material 86 by three polymeric rivets 88. Polymeric rivets 88 may be any polymeric rivet material as described herein, and as illustrated may be considered to be prepared from thermosettable silicone material. Polymeric mesh 84 is joined to biologic material 86, and to another mesh material (not shown) at the other side of biologic material 86, by rivets 88 that contact mesh on both sides of biologic material 86 and extend through three apertures (represented as dashed lines 89) in biologic material 86. The polymeric rivet material is located at the surface of mesh material 84, within interstices (not shown) of mesh material 84, and within apertures 89 (dashed lines) of biologic material 86. Rivets 88 can be prepared from silicone polymeric rivet material by applying the flowable silicon material at room temperature to a surface of mesh 84 to cause the silicone polymer material to flow into the interstices of mesh 84 materials and the apertures of biologic tissue material 86. The polymeric rivet material was cured, e.g., using high temperature, radiation, etc.

Figure 5C:
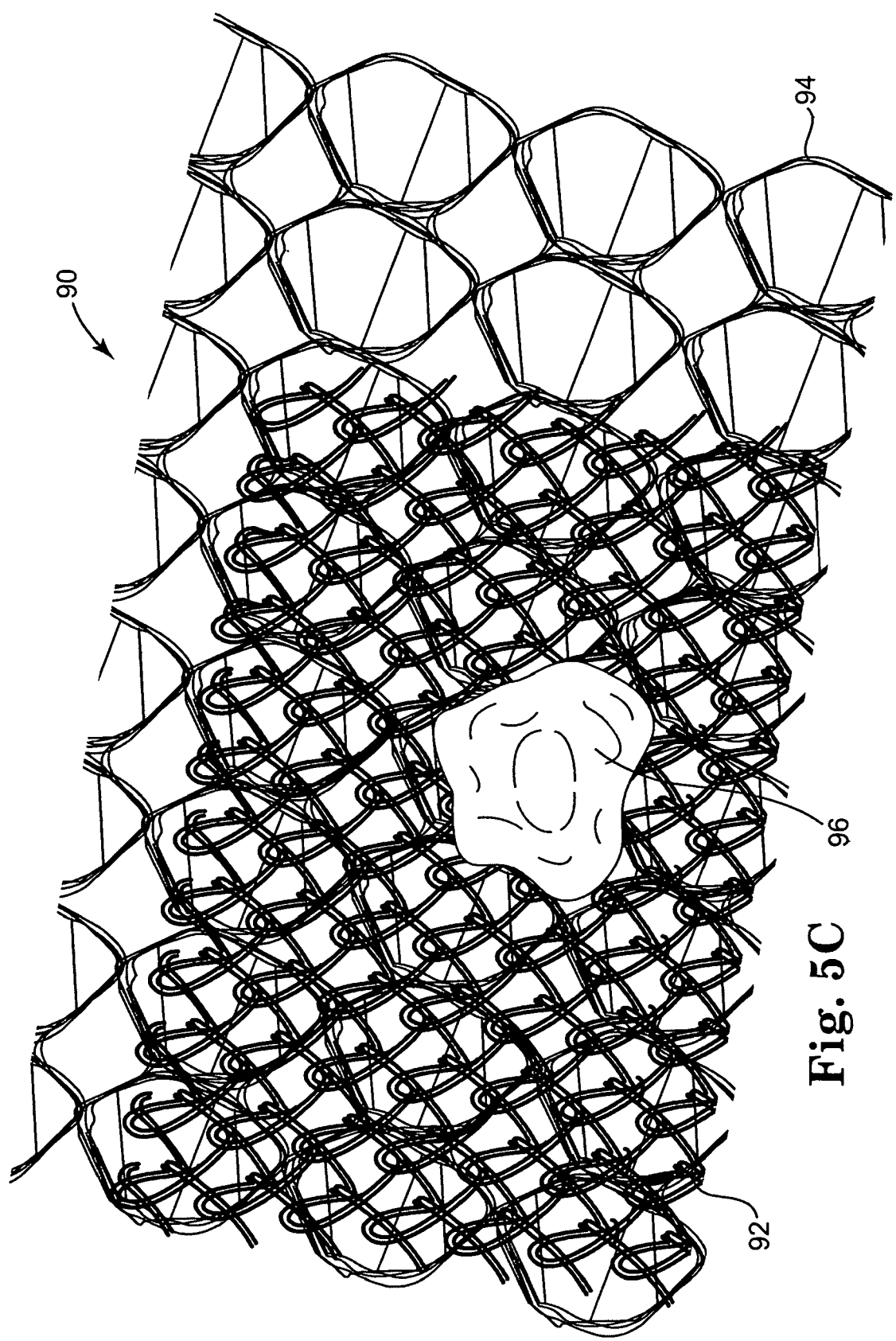
FIG. 5C is a schematic top view of a polymeric rivet and implant according to the invention.

FIG. 5C shows implant 90 that includes polymeric mesh 92 (e.g., polypropylene) joined to a different polymeric mesh, mesh 94 (e.g., polypropylene), by polymeric rivet 96. Mesh 92 has relatively smaller interstices compared to mesh 94, e.g., due to factors such as a more tightly knit pattern of mesh 92 versus mesh 94. Rivet 96 joins different mesh materials 92 and 94 together by contacting each and penetrating interstices of both mesh materials. (The interstices of the mesh materials that contain rivet material are not specifically shown.) The polymeric material of rivet 96 can be any useful polymeric rivet material as described herein, e.g., a thermoplastic or thermosettable polymer. As illustrated, the material of polymeric rivet 96 can be a curable silicone polymeric material that can be prepared to form rivet 96 by being applied to mesh materials 92 and 94 in a manner whereby the polymeric rivet material (e.g., silicone) flows into the interstices of the mesh materials and is then cured or solidified as desired.

Examples of implants that can incorporate a rivet as described include various implants useful to treat conditions of the male and female pelvic floor. These implants may be used to support pelvic tissue such as the rectum, urethra, vagina, etc., to treat a condition such as male or female urinary or fecal incontinence, vaginal prolapse, enterocele, rectocele, cystocele, vaginal vault prolapse, and other pelvic tissue disorders. Many implants useful to treat a pelvic condition can include two pieces of the same or different types of biocompatible materials, joined together, often including a support portion to support or contact a pelvic tissue attached to an extension portion (e.g., an "appendage" or "extension") that extends from the support portion to connect the support portion to a different component of the patient's anatomy. Many examples are described, e.g., in U.S. application No. 2004/0039453 "Pelvic Health Implants and Methods," having Ser. No. 10/423,662, and filed on Apr. 25, 2003; U.S. application Ser. No. "Method and Apparatus for Treating Pelvic Organ Prolapse," having Ser. No. 10/834,943, and filed on Apr. 30, 2004; and U.S. application No. 2003/0171664 "Transobturator Surgical Articles and Methods," having Ser. No. 10/306,179, and filed on Nov. 27, 2002.

Figure 5D:
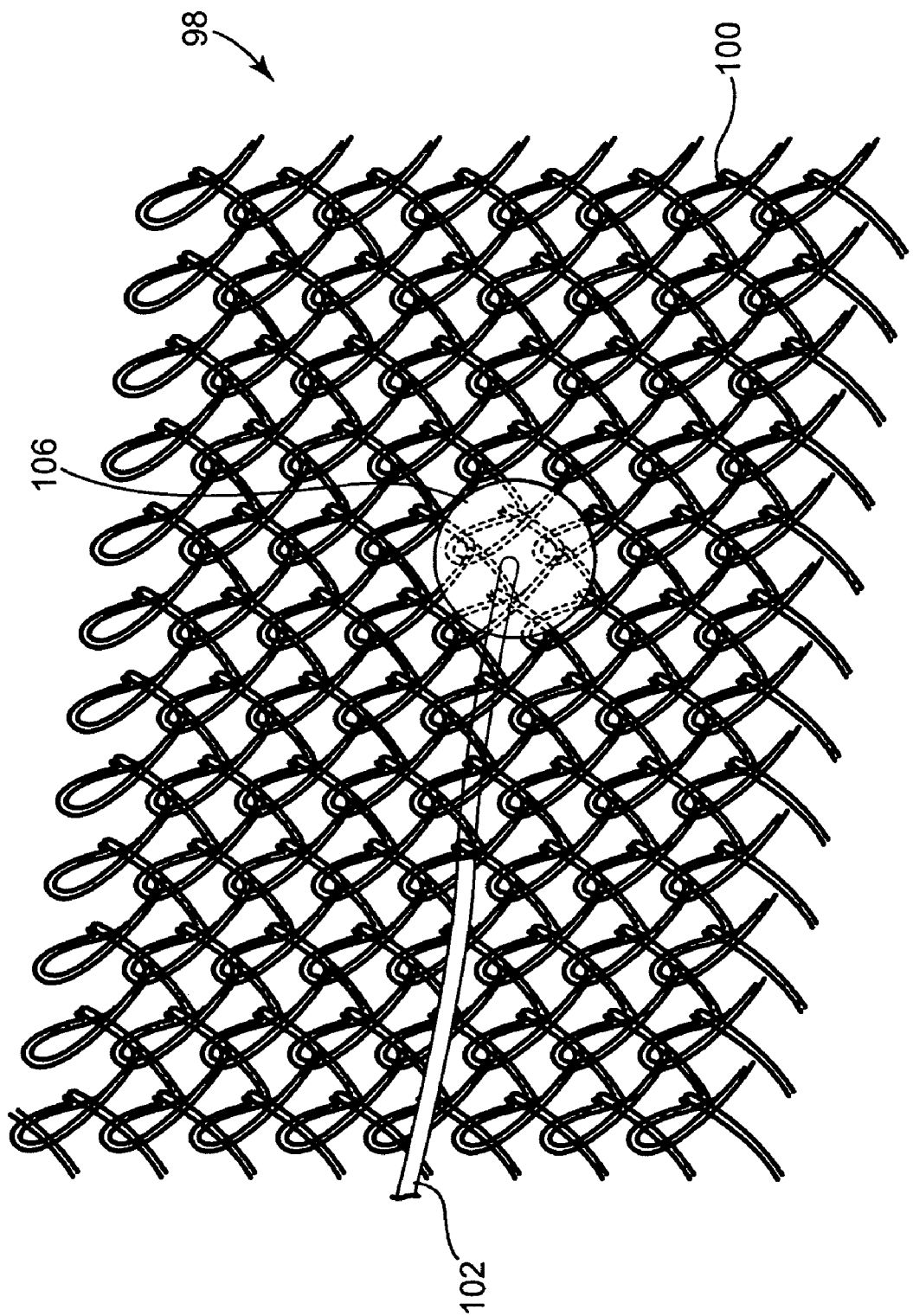
FIG. 5D is a schematic top view of an implant of the invention that includes materials connected by a polymeric rivet.

In some embodiments of the invention, and as illustrated at FIG. 5D, implant materials may involve a suture joined to synthetic or non-synthetic material. As an advantage of such a use of a polymeric rivet, the suture can be attached without the need to tie a knot. In general, a flowable (e.g., thermoplastic or curable) polymeric rivet material could be caused to flow to contact both the suture and an implant material, with flow of the polymeric rivet material between interstices or holes of the implant material. The polymeric rivet material may then be solidified or cured. A suture could be attached using a polymeric rivet to any of various commercially available surgical implants, such as those useful to treat pelvic conditions, e.g., commercially available products from American Medical Inc., of Minnetonka Minn., including SPARC®, MONARC™, BIOARC™, PERIGEE™, and APOGEE™ products; Sacrocopoplexy Y-Mesh (SRAIGHT-IN™) products (e.g., surgical devices); as well as other graft-augmented implantable surgical devices.

FIG. 5D shows an embodiment of an implant, implant 98, which includes polymeric rivet 106 that joins suture 102 to an implant material illustrated as mesh 100. In this illustration, dashed lines are indicated within rivet 106 to show how strands of polymeric mesh 100 define interstices that contain polymeric rivet material that makes up rivet 106. Implant 98 is illustrated as only including mesh 100, suture 102, and rivet 106. Optionally, implant 100 could include another implant material such as another synthetic (e.g., mesh) or a biologic material, e.g., joined to mesh 100 and suture 102 by rivet 106. Polymeric rivet 106 was formed by applying a flowable polymer to mesh 100 and suture 102 in a manner that caused the polymeric rivet material to flow into the interstices of the mesh material while also contacting the suture. The polymeric rivet material solidified, e.g., if thermoplastic, the melted, flowable polymeric rivet material, after application, was cooled; and if otherwise curable, the flowable polymeric rivet material, after application, was exposed to a condition to cause cure, such as elevated temperature or radiation.

Exemplary implants useful for treating pelvic conditions may include the same or different materials attached using a polymeric rivet, e.g., any of synthetic mesh, a suture, or a biologic material, attached together. Many pelvic implants generally include a support portion having a size and shape to attach to a location proximal to a pelvic tissue (e.g., urethra, bladder, rectum, or vagina). The support portion may be of a biologic material or a synthetic (e.g., mesh) material. Attached to the support portion can be one or two extensions (or "extension portions" or "end portions"), the extensions shaped and sized to extend from the point of attachment with the support portion of the implant to another location to be secured. Each extension may be an elongate material that is biologic or synthetic, e.g., an elongate synthetic mesh attached directly to the support portion. Each of the materials can include some form of hole or aperture sized to receive a polymeric rivet material, to join the extension portion to the support portion.

According to certain embodiments of implants, various additional components and features can be incorporated into a useful implant, such as components and features that facilitate installation of a device during a surgical procedure. For instance, a suture, as mentioned above, may be attached to an implants for use in adding tension or in positioning the implant or a portion (e.g., extension) of the implant. Alternately or in addition, an exemplary implant may include a removable sheath such as a plastic, transparent elongate tube, that can cover extension portions of an implant to facilitate installation by allowing a surgeon to apply tension or pressure on the sheath to indirectly apply pressure or tension to the extension portion. Additionally or alternately, extension members of an implant may include a connector or "dilator" tip at the end of the extension member distal from the support member, the connector being able to cooperate with an insertion tool during a surgical procedure to either push or pull the connector using the end of the insertion tool. For example, a tip may be a rigid plastic tip constructed to attach to an end of an elongate tool by snapping or otherwise securing to the end of the tool. The tool can then be used to push or pull the connector through a tissue passage to also bring the extension portion of the implant through the tissue passage.

Illustrations of an exemplary pelvic implant are at FIGS. 6 and 6A, which depict an implant useful as a prolapse support device, e.g., for treating vaginal prolapse. FIG. 6 is a front view and FIG. 6A is a side view. Implant 110 includes end portions 114 and 116 connected to central support portion 118 by polymeric rivets 112. Sutures 118 extend along the lengths of each of extension 114 and 116 and are connected to central support portion 118 and extensions 114 and 116 by the same rivets 112. Not shown as included with implant 110 are optional features of a pelvic implant such as tips at each of the non-attached ends of extension portions 114 and 116, which optional tips could be adapted to connect to an end of an installation device or tool such as a needle, and protective flexible covers or sheaths that could extend over and contain extensions 114 and 116.

Figure 7:
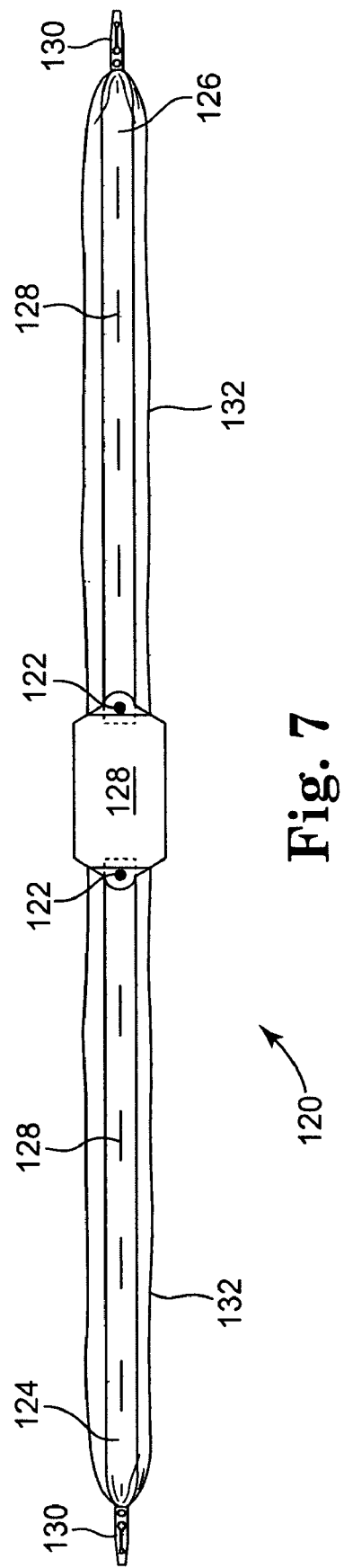
FIG. 7 is a schematic top view of a pelvic implant of the invention that includes materials connected by a polymeric rivet.

An illustration of another exemplary pelvic implant is at FIG. 7, showing implant 120 that can be useful as a pelvic implant, e.g., for treating urinary incontinence. Implant 120 includes end portions 124 and 126 connected to central support portion 128 by polymeric rivets 122. Sutures 128, which are optional and not required, extend along the lengths of each of extension 124 and 126 and are connected to central support portion 128 and extensions 124 and 126 by the same rivets 122. Also shown in this exemplary embodiment are certain optional features of a pelvic implant. Optional tips 130 are attached at each of the non-attached ends of extension portions 124 and 126. Tips 130 can be, e.g., rigid plastic tips that are shaped to connect to an end of an implantation device or tool such as a needle. Also shown are optional sheaths or covers 132, which can be flexible, e.g., transparent covers that extend over the lengths of each of extensions 114 and 116 from rivet 122 to the dilator 130, which is crimped over covers 132. Covers 132 can be useful, e.g., as protection for extensions 124 and 126, and also for installation of implant 120, by being sufficiently stiff and non-elastomeric to allow the extensions to be pulled through a tissue path by pulling on cover 132.

The invention also relates to methods of preparing a surgical implant to include a rivet, such as a polymeric rivet. The methods involve aligning apertures of implant materials and inserting a rivet material from a surface of one of the materials, into interstices or holes of both materials. The rivet material is then processed to join the materials together. Processing a rivet material may involve any type of chemical or mechanical processing, such as a step to cure a chemically or thermally curable polymeric rivet material (e.g., by exposure to heat, radiation, etc.); a temperature change to cure a thermoplastic polymeric rivet material; a step of producing an ultrasonic weld; or a mechanical step such as bending, crimping, turning, twisting, screwing, folding, or otherwise forming a mechanical bond from a rivet material, e.g., to mechanically attach rivet materials to form a rivet.

In general, during the step of inserting a rivet material into holes or interstices of an implant material, a rivet material may be in the form of a solid material or a flowable (e.g., liquid) material. Examples of materials that can be in a solid form when inserted include room temperature solid polymeric materials such as plastics that can be placed together to form a mechanical attachment such as an ultrasonic weld. Examples of materials that are in a flowable (e.g., fluid or liquid) form when inserted include room temperature fluid materials that may be thermosettable or otherwise chemically curable polymeric materials, and room temperature solid thermoplastic polymeric materials that can be heated above room temperature to become flowable, then re-solidified by a temperature reduction.

As an example of a step of inserting a flowable polymeric material into interstices of implant material, a flowable polymeric rivet material (e.g., a curable polymer or a thermoplastic polymer) may be provided in a liquid form. A thermoplastic polymer may require heating to above room temperature, while a chemically or heat curable polymer can be at room temperature. Separately, implant materials are provided that include interstices. The materials may be contacted together with aligned interstices and the flowable polymeric rivet material may be injected or inserted from a surface of a material to flow into the interstices and through a thickness of at least one material, optionally through the total thickness of two or more implant materials to form a rivet shaft. Optionally, the rivet material may be shaped to form one or two rivet heads at one or more exterior surfaces of the implant.

Various modes of inserting a rivet material into interstices of implant material will be appreciated, using various equipment and processing techniques that are presently known or that may be developed in the future. For example, a flowable polymeric rivet material can be pressurized and injected into interstices of implant materials with the use of equipment that causes pressurized flow of the material, e.g., a device such as a glue gun, hot glue dispenser, extruder, etc. A polymeric rivet material may be injected into interstices of implant material then be solidified (e.g., cured or allowed to cool) to mechanically join the material.

The invention also relates to apparatus for making an implant having a polymeric rivet, such as a mold, an injector or "microinjector," and combinations of a mold and injector.

Generally, a useful mold may include closeable surfaces sized to contain pieces or portions of surgical implant material such as an extension portion to be joined to a support portion, each portion having apertures through which polymeric rivet material will be placed. The apertures can be aligned when the closable surfaces are closed to contain the material. One of the closeable surfaces includes a port that also aligns with the apertures.

Molds of the invention can optionally include one or more gaskets located within the mold to define a portion of space used to form a rivet. A gasket can be included, e.g., circumferentially around an injection port, to contact material of the implant when the implant material is contained by the closed mold. A gasket can be used to control the flow and positioning (i.e., placement) of a fluid rivet material as the rivet material is being applied to (e.g., injected into) implant material.

For example, a mold could include a grommet, gasket, or other type of insert or flow-control structure that, when the mold is closed over material of a surgical implant, would control the flow of flowable polymeric rivet material. The flowable polymeric rivet material could be isolated to a specific area or space of implant material to which the flowable material is applied. Optionally, the same insert or flow-control structure may function to compress one or more materials of the surgical implant during formation of the polymeric rivet. For example, a gasket used to compress an annular surface of mesh material against a biologic material could seal off an area of the mesh within the annular gasket, to prevent flow of polymeric rivet material outside of that area, such as to prevent lateral flow of polymeric rivet material through interstices of the mesh over a larger than desired area, which may not necessarily add to the strength of the polymeric rivet. Control of the flow of the polymeric rivet material in this way could allow the polymeric rivet to be formed into a desired shape and size, e.g., in a generally cylindrical shape, in a way that would increase the strength of attachment between implant materials and minimize the amount of rivet material required.

A gasket may desirably be of any useful material. Examples of desirable gasket materials may include elastomeric or compliant material such as a "soft durometer" material. Exemplary soft durometer materials can include polymeric materials such as natural or synthetic rubbers, silicones, curable polymeric materials such as polyurethanes, and the like. The polymeric material may be a homopolymer, copolymer, or blends or mixtures of homopolymers and copolymers. Materials that are considered to exhibit a soft durometer include materials (e.g., polymeric materials) that exhibit a hardness that falls within the Shore A hardness range, such as a hardness of, e.g., 15 to 30 durometer, e.g., 20 durometer.

Considered by function, a useful gasket material can be of a hardness that, when the closeable surfaces of the mold are closed to contain implant material or materials, gasket and implant material will contact each other and in combination will conform to form a substantially sealed space within which a liquid polymeric material can be injected to form the polymeric material into a polymeric rivet.

Figure 8A:
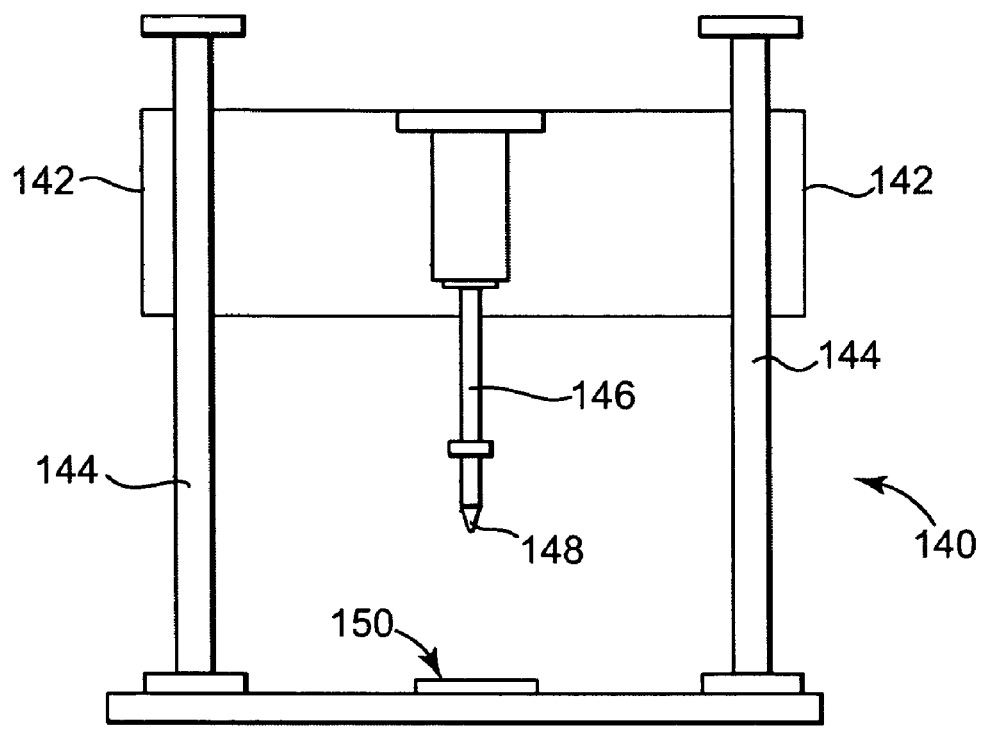
FIG. 8A illustrates an embodiment of an injector for use according to the invention.
Figure 8B:
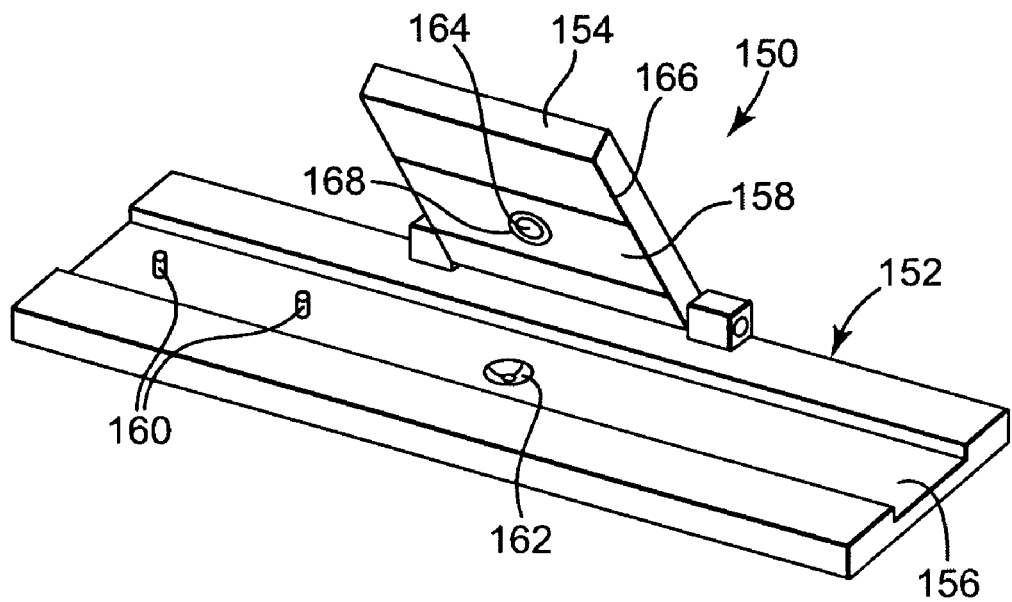
FIG. 8B illustrates an embodiment of an injection mold for use according to the invention.

FIGS. 8A and 8B illustrate embodiments of equipment for use in preparing some embodiments of implants described herein, by injecting a flowable polymeric rivet material into interstices of implant material. These specialized apparatus include features such as an insert mold (for holding pieces or portions of an implant for joining), an injection assembly for injecting a flowable polymeric material into interstices of implant material or materials, and related structures and appurtenances such as a linear slide, air cylinder, nozzle, etc.

Particular injection assembly apparatus for use in injecting polymeric material as a polymeric rivet may include features that make the injector especially suitable for assembling implants as described herein, e.g., on a relatively small or relative low-speed commercial scale as opposed to high-speed commercial injection scale. Injection apparatus of the invention can avoid high temperatures based on the desire to avoid damage or degradation of synthetic or non-synthetic implant materials, while still obtaining a solid rivet attachment between two implant materials.

To avoid degradation or damage to implant material, injection apparatus of the invention can operate at relatively low temperature, such as below 500 degrees Fahrenheit, e.g., below 450 degrees Fahrenheit, such as between about 350 degrees Fahrenheit and 450 degrees Fahrenheit.

Also useful to prepare an implant as described herein is precise control of the speed (flow rate) and amount (i.e., total volume) of a flowable polymeric material injected as a polymeric rivet. Flow rate and total volume can also affect whether implant material becomes damaged during injection of a heated thermoplastic material. Further, precise control of flow rate and total volume can allow for precise formation in terms of size and shape of a polymeric rivet prepared from a flowable polymeric rivet material. Injection apparatus of the invention can allow for high precision control of flow rate and total injected volume of flowable polymeric material, in forming a polymeric rivet.

Useful total injected volume of flowable rivet material can be any volume useful to form a rivet as described. Exemplary rivet dimensions may include a height that is the same as the total thickness of the implant materials being bonded together, or slightly greater to produce a rivet head if desired. Optionally, a rivet head may extends above or below the thickness of the implant material, e.g., by a distance of up to 0.03 inches, e.g., up to 0.01 inches. A width of a rivet (e.g., shaft) may be as desired, and may depend on factors such as the number of rivets used, e.g., a single rivet or multiple rivets. Generally, a rivet shaft may have a width in the range from about 0.01 to about 0.10 inches in diameter, e.g., from about 0.04 to about 0.08 inches in diameter. If a rivet head is included, an exemplary size of a rivet head may be from about 2 to about 5 times the diameter of the rivet shaft.

An exemplary range of total volume of flowable polymeric material required to form a polymeric rivet, can depend on the number and size of rivets, and whether a rivet head is formed. For a rivet that joins mesh to mesh, a rivet head may not be necessary and a smaller total volume of polymeric material may be used compared to embodiments of implants that include a rivet head, e.g., to secure a biologic material to a mesh. Exemplary amounts of rivet material useful to form a rivet (optionally including a rivet head or heads) can be amounts in the range from about 0.001 cubic centimeters to about 0.1 cubic centimeters, e.g., from about 0.003 cubic centimeters to about 0.05 cubic centimeter.

High precision of flow rate and volume during rivet formation can be accomplished, for example, by use of an injector unit with a small diameter injection barrel (e.g., 0.125 to 0.5 inch diameter, such as 0.25 inch diameter) and a small injector nozzle (0.060 inch diameter) that delivers less than about 0.1 cubic centimeters, e.g., up to about 0.05 cubic centimeters of material, with injection relatively low injection forces, e.g., injection forces in the range from about 20 to 60 pounds, such as from about 35 to about 40 pounds.

Referring to FIG. 8B, there is illustrated an insert mold 150 specially designed to produce a polymeric rivet from a flowable polymeric rivet material. Mold 150 includes base 152 and hinged gate 154. Hinged gate 154 is closeable relative to base 152 such that gate 154 can be closed over base 152 while implant material (not shown) is located within channel 156 of base 152 and opposing channel 158 of gate 154. Optional mesh holding pins 160 are shown within channel 156. Pins 160 can be inserted into or through interstices of a mesh material located within channel 156 to maintain a desired position of a mesh material during injection of a polymeric rivet material. Base 152 includes round depression 162, which aligns with injection port 164 of gate 154. Depression 162 is shown to be round but may be any shape desired to form a portion (e.g., head) of a polymeric rivet. Gasket 168 is located around the periphery of port 164, of gate 154.

Figure 8C:
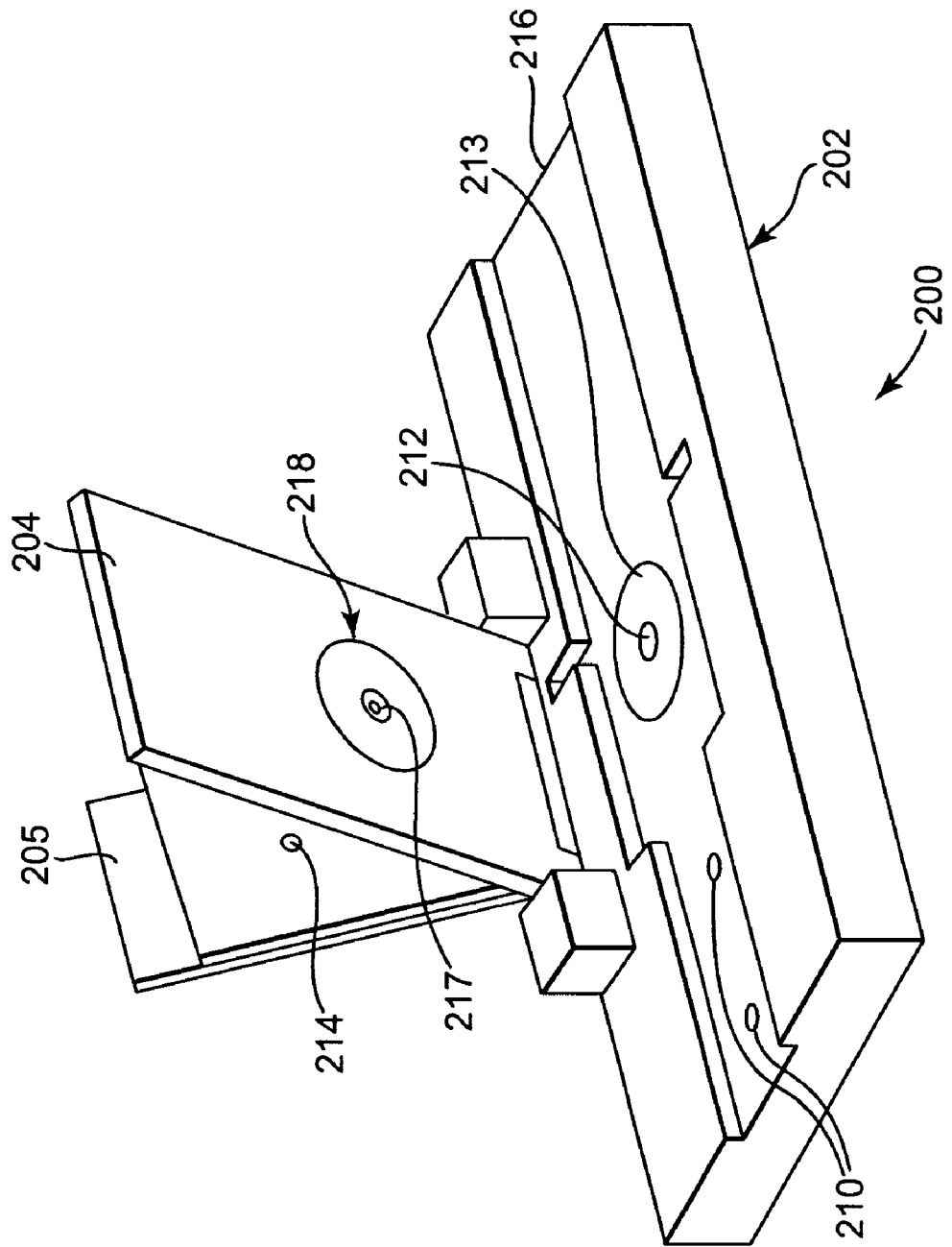
FIG. 8C illustrates an embodiment of an injection mold for use according to the invention.

Referring to FIG. 8C, there is illustrated another embodiment of an insert mold, mold 200. Mold 200 includes base 202 and hinged gates 204 and 205. Hinged gates 204 and 205 are closeable relative to base 202 such that gates 204 and 205 can be closed over base 202 while implant material (not shown) is located within channel 216 of base 202. Optional holding orifices 210 are shown within channel 216. Orifices 210 can be aligned with interstices of implant material and pinned or otherwise secured to a desired location within channel 216 to maintain a desired position of an implant material during injection of a polymeric rivet material. Space 212 is defined in part by gasket 213 and in part circumferentially by a surface of based 202. Space 212 aligns with injection port 214 of gate 205, and with orifice 217 inside of gasket 218 of gate 204. Space 212 may optionally include a depression within the surface of base 202. In use, one or two pieces or portions of implant material (not shown) can be placed in channel 216 of base 202. Apertures of implant material can be aligned and the aligned apertures can be placed over space 212 such that when gates 204 and 205 are closed, the implant material apertures also align with apertures 214 and 217 of gates 205 and 204. A flowable polymeric rivet material can then be injected through injection port 214 and flow through aperture 217, with the implant material being positioned to receive the polymeric rivet material at a desired location for polymeric rivet formation.

A flowable polymeric rivet material can be injected to form a polymeric rivet, using a mold such as mold 150 or 200, by use of any desired injection or extrusion apparatus, for example an apparatus as illustrated in any of FIG. 8A, or similar or different but otherwise useful apparatus. FIG. 8A shows an example of an injector useful to inject a polymeric material, e.g., through aperture 164 of injection gate 154 of mold 150, to form a polymeric rivet. FIG. 8A illustrates a microinjection molding machine ("microinjector") 140. Microinjector 140 is referred to as a "microinjector" because the apparatus operates at a scale useful to hand assemble surgical devices by injection of flowable polymeric material, with precisely controlled flow rates and total volumes. Microinjector 120 operates at one or a combination of operating parameters selected from a temperature in the range from 350 to 500 degrees Fahrenheit, e.g., from 400 to 450 degrees Fahrenheit; a single injection volume of injected material in the range from about 0.001 cubic centimeters to about 0.10 cubic centimeters, e.g., from about 0.003 cubic centimeters to about 0.05 cubic centimeter; and can include a small diameter injection barrel (e.g., 0.125 to 0.5 inch diameter, such as 0.25 inch diameter) and a small injector nozzle (e.g., having a diameter the range from about 0.01 to about 0.10 inches in diameter, e.g., from about 0.04 to about 0.08 inches in diameter, or about 0.060 inch diameter) that delivers less than 0.1 cubic centimeters of material with an injection force of less than 50 pounds.

Referring to FIG. 8A, microinjector 140 includes linear slide 142 that can be driven (e.g., pneumatically, hydraulically, or electrically, etc.) up and down along supports 144 to raise or lower slide 142. Attached to slide 142 is injector assembly 146 and injector head/nozzle 148.

End of nozzle 148 is shaped and sized to fit against a mold, e.g., mold 150 (alternately mold 200) at gate 154, to align with aperture 164 (i.e., at the outside surface of gage 154 when gate 154 is closed) and to inject polymer from nozzle end 148 through aperture 164 and into mold 150 to form a polymeric rivet. The size and shape of the polymeric rivet will be defined by features of the mold such as the size and shape of depression 162 and gasket 168, and the total volume of polymeric rivet material injected from the injector 140.

An example of a method of joining a two-piece mesh (e.g., a "Y-mesh") material to a biologic material by a molding process that can include the mold of FIG. 8B, can include steps such as the following:

1. Punch hole in a piece of biologic tissue material
2. Place the punched end of the biologic material strip between pieces of the "Y-mesh" and center the punched end at a location that will be beneath the injection gate aperture 164.
3. While placing the assembled "Y-mesh" and biologic materials into the injection mold, locate and secure the mesh portion using mesh holding pins 160.
4. Close the mold top 154 with the hole in the biologic material centered beneath the injection gate aperture 164.
5. Place the mold into an injection molding machine that dispenses a flowable polymeric rivet material, with aperture 164 centered under an injector nozzle of the injection molding machine. Load the injector assembly with a polymeric rivet material (e.g., a thermoplastic polypropylene).
6. Cycle press:
   The linear slide advances down so the heated nozzle locates into the mold injection gate
   The thermoplastic polymeric rivet material is injected into the mold
   The linear slide returns to the up position
7. Remove the mold from the molding machine, open the gate, and remove the assembly that includes the mesh material joined to the biologic material by a polymeric rivet
8. Trim the assembly as needed The methods and devices described herein could be used for various surgical procedures, as will be understood by those of skill, including any of various methods relating to pelvic prolapse repair, such as treatment of specific prolapse and incontinent conditions. As will also be appreciated by those of skill, the invention will be useful with other general and specific surgical procedures and surgical implants that involve joining one material to another (e.g., a biologic tissue material to a polymeric material), including devices and methods useful for hernia repair, cosmetic surgery, and others.

The invention claimed is:

1. A surgical implant comprising a support portion and an elongate extension portion extending from the support portion, the support portion and the elongate extension portion comprising a material selected from a synthetic mesh material, a synthetic film material, and a biologic material, and being joined by a polymeric rivet, the polymeric rivet being located within apertures of the support portion and the extension portion and extending through a thickness of at least one of the support portion and the elongate extension portion, wherein the implant is capable of being used as a urethral support, a rectal support, or a vaginal prolapse support, wherein the polymeric rivet comprises thermoplastic having a processing temperature in the range from 350 to 500 degrees Fahrenheit.

2. The implant of claim 1, wherein the extension portion comprises a synthetic mesh material or a synthetic film material selected from a solid or semi-solid film, a braided material, a knit material, a tied material, a mesh, a woven material, and a non-woven fabric-type material.

3. The implant of claim 1, wherein the support portion comprises biologic material and the extension portion comprises synthetic mesh material.

4. The implant of claim 3, wherein
the support portion comprises biologic material having a formed aperture,
the extension portion comprises synthetic mesh material, and
the polymeric rivet comprises a molded shaft that extends from a surface of the synthetic mesh material through interstices in the synthetic mesh material and through the formed aperture.

5. The implant of claim 4, wherein
the extension portion comprises two aligned pieces of synthetic mesh material, and the formed aperture of the biologic material is located between the two aligned pieces of synthetic mesh, and
the polymeric rivet comprises a molded shaft that extends from a surface of a first piece of synthetic mesh material, through interstices in the first piece, through the formed aperture, and through interstices of a second piece of synthetic mesh material.

6. The implant of claim 1, wherein the polymeric rivet comprises a thermoplastic polyolefin material.

7. The implant of claim 1, comprising
a support portion
two extension portions attached to the support portion by polymeric rivets,
a dilator at ends of each of the extension portions, and
insertion sheaths covering each extension portion.

8. The implant of claim 7, wherein the support portion comprises biologic material and the extension portions comprise synthetic mesh material.

9. The implant of claim 1, wherein the polymeric rivet comprises a molded shaft that extends from one surface of the implant, through a full thickness of the implant, and to another surface of the implant.

10. The implant of claim 9 wherein the polymeric rivet includes two rivet heads at opposing surfaces of the implant.

11. A surgical kit comprising the implant of claim 1 and an insertion tool.

12. The kit of claim 11, wherein the implant is selected from a urethral support, a rectal support, and a vaginal prolapse support.

13. A method of forming or assembling a surgical implant, the method comprising
    providing portions of implant material, each portion comprising an aperture,
    contacting the portions of implant material with the apertures aligned,
    inserting a polymeric rivet material from a surface of either implant material, the polymeric rivet material extending into the apertures, and
    processing the polymeric rivet material to attach the implant materials.

14. A method of forming or assembling a surgical implant, the method comprising
    providing a support portion comprising a material selected from a synthetic mesh material, a synthetic film material, and a biologic material, and comprising a support portion aperture,
    providing an extension portion comprising a material selected from a synthetic mesh material, a synthetic film material, and a biologic material, and comprising an extension portion aperture,
    contacting the extension portion and the support portion with aligned extension portion aperture and support portion aperture,
    inserting a polymeric rivet material from a surface of either the extension portion or the support portion, the polymeric rivet material extending into the extension portion aperture and the support portion aperture, and
    processing the polymeric rivet material to attach the extension portion to the support portion, wherein the polymeric rivet comprises thermoplastic having a processing temperature in the range from 350 to 500 degrees Fahrenheit.

15. The method of claim 14, wherein the polymeric rivet material is a thermoplastic polymeric material, the method further comprising inserting the polymeric rivet material as heated flowable polymeric rivet material and allowing the inserted polymeric rivet material to solidify to attach extension portion to support portion.

16. The method of claim 15, further comprising using a mold to maintain contact between extension portion and support portion, wherein the mold defines a space for injecting flowable polymeric rivet material into interstices of the extension portion and the support portion.

17. An insert mold adapted to assemble materials of a medical implant, the mold comprising
    closeable surfaces sized to contain portions of implant material, each portion comprising an aperture,
    a surface comprising an injection port adapted to be aligned with the apertures,
    a gasket,
    wherein when the closeable surfaces are closed to contain the implant material with aligned apertures, the gasket partially defines a space that contains the aligned apertures.

18. An insert mold according to claim 17, comprising
    closeable surfaces sized to contain surgical implant material comprising and end portion and a support portion, the end portion comprising an end portion aperture and the support portion comprising a support portion aperture,
    a surface comprising an injection port adapted to be aligned with the end portion aperture and the support portion aperture,
    a gasket,
    wherein when the closeable surfaces are closed to contain the end portion and the support portion, with aligned apertures, the gasket partially defines a space that contains the aligned apertures.

19. The mold of claim 17, wherein the gasket has a hardness in the Shore A range.

20. Apparatus comprising, in combination, the insert mold of claim 17 and a microinjector, the microinjector:
    operating at a temperature in the range from 350 to 500 degrees Fahrenheit;
    producing a single injection volume of injected material in the range from about 0.001 cubic centimeters to about 0.1 cubic centimeters, and
    including an injection barrel having a diameter in the range from about 0.125 to 0.5 inches, and an injector nozzle having a diameter in the range from about 0.01 to about 0.10 inches.

21. A method of producing a surgical implant, the implant comprising a support portion and an elongate extension portion extending from the support portion, the support portion and the elongate extension portion being joined by a polymeric rivet, the polymeric rivet being located within apertures of the support portion and the extension portion and extending through a thickness of at least one of the support portion and the elongate extension portion, wherein the implant is capable of being used as a urethral support, a rectal support, or a vaginal prolapse support,
    the method comprising
        providing an extension portion of an implant comprising an extension portion aperture,
        providing a support portion of an implant comprising a support portion aperture,
        using an insert mold according to claim 17 to contact the extension portion and the support portion with aligned extension portion aperture and support portion aperture, and
        using an injector assembly to inject flowable polymeric material into the extension portion aperture and the support portion aperture.

22. The method of claim 21, wherein one or more of the extension portion and the support portion comprises a synthetic mesh material, and wherein the method comprises compressing the synthetic mesh material by contacting the mesh material with the gasket.

23. A surgical implant comprising implant materials joined by a polymeric rivet, the polymeric rivet extending from a surface of the implant, though apertures of at least two portions of implant material, wherein
    the two portions of implant material comprise an extension portion and a support portion,
    the extension portion comprises a synthetic material selected from a solid or semi-solid film, a braided material, a knit material, a tied material, a mesh, a woven material, and a non-woven fabric-type material, and
    the support portion comprises a material selected from
        a biologic material and
        a synthetic material selected from a solid or semi-solid film, a braided material, a knit material, a tied material, a mesh, a woven material, and a non-woven fabric-type material,
    wherein the polymeric rivet comprises thermoplastic having a processing temperature in the range from 350 to 500 degrees Fahrenheit.

24. The implant of claim 23 wherein the polymeric rivet comprises a thermoplastic polyolefin.

25. The implant of claim 23 wherein the polymeric rivet includes two rivet heads at opposing surfaces of the implant.

26. The surgical implant of claim 1 wherein the synthetic mesh material and the synthetic film material comprise polymeric fibers.

27. The surgical implant of claim 14 wherein the synthetic mesh material and the synthetic film material comprise polymeric fibers.

28. The surgical implant of claim 23 wherein the synthetic mesh material and the synthetic film material comprise polymeric fibers.

29. The implant of claim 26 wherein the extension portion comprises a synthetic mesh material or a synthetic film material selected from a solid or semi-solid film, a braided material, a knit material, a tied material, a mesh, a woven material, and a non-woven fabric-type material.

30. The implant of claim 27 wherein the extension portion comprises a synthetic mesh material or a synthetic film material selected from a solid or semi-solid film, a braided material, a knit material, a tied material, a mesh, a woven material, and a non-woven fabric-type material.

31. The implant of claim 28 wherein the extension portion comprises a synthetic mesh material or a synthetic film material selected from a solid or semi-solid film, a braided material, a knit material, a tied material, a mesh, a woven material, and a non-woven fabric-type material.

32. The surgical implant of claim 1 wherein the polymeric rivet is molded.

33. The surgical implant of claim 29 wherein the molded polymeric rivet comprises a shaft that extends from one surface of the implant, through a full thickness of the implant, and to another surface of the implant.

34. The surgical implant of claim 30 wherein the molded polymeric rivet further comprises a rivet head attached to the shaft.

35. The method of claim 16, wherein the space defined by the mold is shaped such that a polymeric rivet formed in the space comprises a shaft that extends from one surface of the implant, through a full thickness of the implant, and to another surface of the implant.

* * * * *

UNITED STATES PATENT AND TRADEMARK OFFICE
CERTIFICATE OF CORRECTION

| | | |
|---|---|---|
| PATENT NO. | : 7,722,527 B2 | Page 1 of 1 |
| APPLICATION NO. | : 11/115655 | |
| DATED | : May 25, 2010 | |
| INVENTOR(S) | : Mark S. Bouchier et al. | |

It is certified that error appears in the above-identified patent and that said Letters Patent is hereby corrected as shown below:

Column 4, line 18, "mat" should be -- may --.
Column 5, line 14, delete "a" (second occurrence).
Column 6, line 40, delete "the"; column 6, line 42, delete "portions".
Column 10, line 50, delete "a"; column 10, line 53, after "portion" insert -- of --; column 10, line 59, "extend" should be -- extends --; column 10, line 60, delete "do".
Column 11, line 35, delete "a".
Column 12, line 12, "show" should be -- shown--; column 12, line 38, after "can" insert -- be --; column 12, line 38, delete "mesh" (first occurrence).
Column 13, line 42, delete "Ser. No.".
Column 14, line 40, "implants" should be -- implant --.
Column 17, line 52, "extends" should be -- extend --; column 17, line 67, delete "used".
Column 18, line 13, delete "injection".
Claim 23, column 22, line 51 "though" should be -- through --.

Signed and Sealed this

Nineteenth Day of April, 2011

David J. Kappos
*Director of the United States Patent and Trademark Office*